(12) United States Patent
Irie et al.

(10) Patent No.: US 6,471,711 B2
(45) Date of Patent: Oct. 29, 2002

(54) DEVICE FOR GUIDING PUNCTURE NEEDLE

(75) Inventors: Toshiyuki Irie, Ibaragi-ken; Yuji Itai, Tokyo; Masaru Maruyama, Nagano-ken, all of (JP)

(73) Assignee: Hakko Electric Machine Works, Co. Ltd., Nagano-Ken (JP)

( * ) Notice: Subject to any disclaimer, the term of this patent is extended or adjusted under 35 U.S.C. 154(b) by 0 days.

(21) Appl. No.: 09/969,901

(22) Filed: Oct. 3, 2001

(65) Prior Publication Data

US 2002/0082611 A1 Jun. 27, 2002

Related U.S. Application Data

(63) Continuation-in-part of application No. 09/372,304, filed on Aug. 11, 1999, now abandoned.

(30) Foreign Application Priority Data

Aug. 11, 1998 (JP) .......................................... 10-226405
Aug. 2, 1999 (JP) .......................................... 11-218978

(51) Int. Cl.$^7$ .............................................. A61B 19/00
(52) U.S. Cl. ..................................................... 606/130
(58) Field of Search ........................... 606/130, 96, 97; 604/115, 116, 117; 600/562–580

(56) References Cited

U.S. PATENT DOCUMENTS

| | | | |
|---|---|---|---|
| 1,831,813 A | | 11/1931 | Levedahl |
| 2,235,419 A | | 3/1941 | Callahan et al. |
| 2,705,949 A | | 5/1955 | Silverman |
| 3,964,480 A | | 6/1976 | Froning |
| 4,733,661 A | | 3/1988 | Palestrant |
| 4,744,353 A | | 5/1988 | McFarland |
| 5,056,523 A | | 10/1991 | Hotchkiss, Jr. et al. |
| 5,163,430 A | * | 11/1992 | Carol ...................... 125/653.1 |
| 5,280,427 A | * | 1/1994 | Magnusson et al. ... 364/413.01 |
| 5,534,005 A | | 7/1996 | Tokish, Jr. et al. |
| 5,569,267 A | | 10/1996 | Howard, III et al. |
| 5,637,074 A | | 6/1997 | Andino et al. |
| 5,669,915 A | | 9/1997 | Caspar et al. |
| 5,728,128 A | * | 3/1998 | Crickenberger et al. ...... 606/97 |

FOREIGN PATENT DOCUMENTS

| | | |
|---|---|---|
| EP | 5 518 397 | 5/1992 |
| JP | 1987-127036 | 6/1987 |
| JP | 7-236633 | 9/1995 |
| JP | 8-238248 | 9/1996 |
| JP | 9-140716 | 6/1997 |

* cited by examiner

Primary Examiner—Eduardo C. Robert
(74) Attorney, Agent, or Firm—Scully, Scott, Murphy & Presser

(57) ABSTRACT

A device for guiding a puncture needle used in CT (computerized tomography) comprises a guide section having an insertion hole for an introducer and the puncture needle, a pole brace having a leg and standing erect in parallel to the guide section, and a beam for connecting the guide section with the pole brace wherein the pole brace or the leg has a function for changing its length along the axial direction thereof, the beam for connecting both the guide section and the pole brace with each other is prepared from a moldable plastic material which allows X-rays to pass through the same in case of radiation into an integrally molded article. The guide section is provided with an openable holding section or a detachable holding section being in parallel to the insertion hole in order that the guiding device can be removed from the introducer and the puncture needle which have been inserted in the insertion hole 12, and further the guide section is provided with a metallic thin sheet which indicates a position of such metallic thin sheet in an image when radiation is made, thereby to-provide the device for guiding a puncture needle which has a simple structure and small number of parts, in which a space sufficient for performing manipulation of a puncturing operation with a needle can be assured, which is easily attached to a subject or a patient by an examiner or an operator, by which an exact puncturing operation can be made with respect to a target site, and further which can be removed from a subject's body surface with leaving the puncture needle as it is after having punctured a target site with the needle.

10 Claims, 16 Drawing Sheets

DEVICE FOR GUIDING PUNCTURE NEEDLE

CROSS REFERENCE TO RELATED APPLICATION

This application is a continuation-in-part application of U.S. application Ser. No. 09/372,304, filed Aug. 11, 1991, now abandoned.

FIELD OF THE INVENTION

The present invention relates to a device for guiding a puncture needle for allowing the needle to precisely reach a target site in a subject or a patient (hereinafter referred simply to as "subject") in accordance with a target determined by image data. The puncturing operation being percutaneously carried out with respect to a pectoral region or an abdominal part of the subject in accordance with a target determined by image data, particularly image data obtained in CT (computerized tomography) scanner and the like.

BACKGROUND OF THE INVENTION

In the case where a puncturing operation is percutaneously performed with respect to a pectoral region or an abdominal part of a subject in accordance with a target determined by image data obtained in CT (computerized tomography) scanner and the like, an examiner or an operator (hereinafter referred to simply as "examiner") confirms a target site, decides a puncturing position, a depth, and a direction (a puncturing route) for a puncture needle, and manipulates the puncture needle so as to reach the target site from the surface of the subject body (hereinafter referred optionally to as "subject's body surface") while confirming a needlepoint of the puncture needle under its image, besides the puncturing operation must be made while maintaining a parallel state with respect to the cross section of such CT image, Particularly, the examiner is requested to reproduce the puncturing route determined in the image to perform the puncturing operation. Accordingly, it is an important point from a viewpoint of manipulation to be performed by the examiner how much exact puncturing operation.

In the case where manipulation for a puncturing operation with a needle is practiced clinically without employing any device for guiding such puncture needle, the operation is carried out in such that a position to be punctured in a subject is marked, a needle tube is calibrated as a navigation mark for a depth, CT-photographing is repeated for adjustment of a direction and necessity of puncturing exactly a target, and a needlepoint of the puncture needle is observed by a monitor under its image.

In this case, if it is difficult to capture exactly a target site and to puncture parallel the target site in conformity with a cross section of its image, such events wherein a needle does not reach a target site by a single try occur frequently. In such case, it is necessary for beginning again the puncturing operation. Furthermore, in a monitor observation during a puncturing operation, it is required to repeat photographing for confirming a position of the puncture needle, so that it is desired for an administration wherein an amount of exposure to radiation is reduced with respect to a subject, and for making an arrangement by which significant burden is not given to the subject by reducing a period of time for examination as much as possible.

In order to eliminate the above described disadvantages, devices for guiding puncture needle which are intended to apply to a pectoral region or an abdominal part of a subject have been proposed. They are, for example, a device provided with an angle gauge which is fixed to an examining table; or a device for holding a biopsy needle on a curved arm in a circular arc shape which is employed by fixing to an examining table (Japanese Patent Laid-Open No. 236633/1995); a device for guiding a puncture needle which is provided with a level, a protractor, and a guide plate for the puncture needle and which is employed by floating the same from an examining table on the basis of horizontal plane as its reference (Japanese Patent Laid-Open No, 127036/1987); or a device wherein a number of strings which are not allowed X-rays to pass through them are stretched in two stages with respect to a tetragonal cylindrical body and which has a holding section for a puncture needle being photographed together with a target site, whereby the target site can be determined on the extension from two points in a visible section (Japanese Patent Laid-Open No. 238248/1996); and the like.

When a puncture needle is pierced in accordance with each guiding mechanism by utilizing any of these devices for guiding puncture needle, it becomes possible to allow a needlepoint of the puncture needle to reach a target in conformity with a cross-sectional plane of its image at a certain degree, and further it is expected to reduce the number of times for photographing.

Recently, an image; can be observed real time while scanning continually sections with development of CT apparatus. Hence, manipulation can be performed while confirming always a needlepoint under CT transmission. Accordingly, it becomes possible to perform relatively easy a puncturing operation with high precision.

On the other hand however, since X-rays are continuously exposed in a gantry of a continuous CT scanning apparatus, an amount of exposure to X-rays is significantly restricted by a law as to prevention of radiation damage due to radioactive isotopes and relative laws and ordinances in practical manipulation, Moreover, an administration for direct exposure to radiation upon an examiner during his (or her) manipulation becomes a problem.

In order to solve such exposure problems, a device wherein a major detection needle is connected perpendicularly to a rod serving as a handle; and a needle holder composed of a needle holding section and a handle disposed in parallel to the needle holding section wherein the handle is disposed away 4 to 7 cm from the holding section (Japanese Patent Laid-Open No.140716/1997) have been proposed. When these devices are used, it is possible to avoid direct exposure to radiation with respect to fingertips of an examiner.

However, according to conventional devices for guiding puncture needle, in a device of the type which is fixed to an examining table, since a guiding device must be fixed to an exact position after deciding a target for puncturing with a needle, there is a problem of requiring a much time before starting a puncturing operation because of such troublesome fixing operation Particularly, if there is a movement of a subject's body during examiner's manipulation, the puncture needle deviates from the target site, and further there is a danger of bending or breaking of the puncture needle in the worst case, because the guiding device is fixed to the examining table. Furthermore, the circular arc-shaped device to be attached to an examining table involves also the same problems as that contained in the above described guiding device. In addition, the device contains a problem of large number of parts, and a problem of a complicated structure.

In a device provided with a level or the like, since it is used in a floating state from an examining table, problems relating to fixation of the above described devices are eliminated. However, it is required that the device must be kept horizontal during examiner's manipulation by the use of the level, In a practical use, there is clinically a rare case where a subject's body surface on which the device is to be placed is maintained in a horizontal state. Accordingly, the device must be kept horizontal by an assistant or the like, but it is difficult to maintain a horizontal state during examiner's manipulation.

In a tetragonally cylindrical device provided with strings which are not allowed X-ray to pass through the same, such a problem wherein the device must be kept horizontal during manipulation by an assistant or the like is eliminated, because the device can be used in such a situation that it has been attached to a subject's body surface, However, such device involves a complicated structure and the number of parts therefore increases.

Moreover, a device for a needle holder which is practiced under CT vision through according to a real time CT apparatus can prevent exposure to radiation upon an examiner, but a grip section is not directly connected with a needle, Further; since a puncturing operation is performed with holding the grip section by an examiner, subtle feeling appearing in the case where the needlepoint of a needle piercing a subject's tissue cannot be transmitted to examiner is fingertips, Furthermore, since an introducer or a puncture needle guide is not used, there is a case where the puncture needle curves in piercing a subject's body, so that an exact puncturing operation becomes difficult. A problem of curved needle is particularly remarkable in case of employing a thin needle; In addition, although a target is captured real time under CT image, it is difficult to allow a needle tube to reach directly a target site along an assumed puncturing route. Thus, there is a problem in that the needle is out of a CT section in some cases, so that the needlepoint cannot be checked on.

On one hand, since the inside of a gantry in CT has a diameter of around 600 mm, a distance extending from the lower end of the gantry to a subject's cuticle in a puncturing section is short in case of performing a puncturing operation under CT image wherein a conventional guiding device as mentioned above is employed. As a result, there are frequently such a case where a puncture needle is hard to be contained in a space defined in the gantry, because of a length of the puncture needle or the guiding device, and such a case where examiner's manipulation is difficult, because of a narrowed space for manipulation.

In such a case as described above, a subject must be once transferred to the outside of the gantry in order to puncture the subject's body with a needle. Moreover, since a needlepoint must be confirmed number of times during manipulation for puncturing operation, the subject is transferred to the inside and the outside of the gantry on all such occasions, so that there is such a problem that the subject is considerably burdened, In such type of a device for guiding a puncture needle as mentioned hereinbefore, there is such a need that in an event where examiner's manipulation is completed as a result of puncturing exactly a target site in a subject's body with a needle, and then, separate manipulation follows while leaving a needle tube as it is, the device for guiding a puncture needle forms clinically an obstacle to the separate manipulation in some cases, so that the guiding device is removed from the subject's body with leaving only the puncture needle, a conventional guiding device could have not coped with such need. Accordingly, such a device for guiding a puncture needle by which only the guiding device can be removed from a subject's body with leaving a needle tube punctured as it is, whereby examiner's manipulation can be easily practiced is strongly desired.

SUMMARY OF THE INVENTION

Accordingly, an object of the present invention is to provide a device for guiding a puncture needle having a simple structure, composed of small number of parts, being capable of maintaining sufficiently a space in which manipulation for a puncturing operation is performed with a needle, and being easily and positively attached to the surface of a subject's body by an examiner.

Furthermore, another object of the present invention is to provide a device for guiding a puncture needle by which a percutaneous puncturing operation can be exactly carried out by a needle with respect to a target site in a subject, besides there is no need of dismounting the subject from a gantry during examiner's manipulation.

Still another object of the present invention is to provide a device for guiding a puncture needle where there is no fear of exposure to x-radiation to an examiner even in a puncturing operation under CT vision, and is removable from the surface of a subject's body leaving only a puncture needle after having punctured a target site in the subject.

According to the first feature of the invention, a device for guiding a puncture needle in the case where a puncturing operation with the needle is performed percutaneously with respect to a target site in a subject in accordance with a target determined by image data obtained in CT (computerized tomography), comprises: a guide section having an insertion hole for an introducer and the puncture needle and metal plates that create artifacts for indicating a puncture route when radiation is applied, a pole brace that changes its length along an axial direction standing erect substantially parallel to the guide section and having a leg for securing the device for guiding a puncture needle to a subject's body surface; and a beam for connecting the guide section with the pole brace.

According to the second feature of the invention, a device for guiding a puncture needle as described in the first feature, wherein:

the guide section and the pole brace connected by means of the beam in which the guide section has a height equal with that of the pole brace, or the guide section has a lower height than that of the pole brace.

According to the third feature of the invention, a device for guiding a puncture needle as described in the first feature, wherein:

the pole brace is disposed at a position being substantially parallel to the guide section standing in an erect state, or two of the pole braces are disposed at positions apart from the guide section with equal distances, respectively.

According to the fourth feature of the invention, a device for guiding a puncture needle as described in the first feature, wherein:

the leg in the pole grace contains a suction leg having a function of suction disk ability by which the device for guiding a puncture needle can be secured to a subject's body surface when placed on the objects body.

According to the fifth feature of the invention, a device for guiding a puncture needle as described in the first feature, wherein:

the beam for connecting the guide section with the pole brace contains a connecting section having a function by which the guide section or the pole brace can be rotated at either of an interconnecting section formed by the guide section and the beam, and an interconnecting section formed by the pole brace and the beam.

According to the sixth feature of the invention, a device for guiding a puncture needle as described in the first feature, wherein:

the interconnecting section formed by the guide section and the beam as well as the interconnecting section formed by the pole brace and the beam are provided, respectively, with a fastening function which can prevent tentatively a movement of the rotatable connecting section to fix a position of the guide section, According to the seventh feature of the invention, a device for guiding a puncture needle as described in the first feature, where in:

the beam for connecting both the guide section and the pole brace is prepared from a moldable plastic material or the like into an integrally molded article.

According to the eighth feature of the invention, a device for guiding a puncture needle as described in the first feature, wherein;

the beam for connecting both the guide section and the pole brace is composed of a molded article made of a plastic material or the like which allows X-ray to pass through the same and does not produce shadow in its image in case of a applying radiation, According to the ninth feature of the invention, a device for guiding a puncture needle as described in the first feature, wherein:

the guide section containing the insertion hole is provided with a holding mechanism of an openable, holding section or of a detachable holding section along the longitudinal direction of the insertion hole in order that the device for guiding a puncture needle can be removed from the introducer and the puncture needle which have been inserted in the insertion hole.

According to the tenth feature of the invention, a device for guiding a puncture needle as described in the first feature, wherein:

The metal plates are positioned in parallel and opposite each other on the guide section for creating parallel artifacts.

BRIEF DESCRIPTION OF THE DRAWINGS

The present invention will be explained in more detail in conjunction with appended drawings, wherein.

DESCRIPTION OF THE PREFERRED EMBODIMENTS

Figure 1:
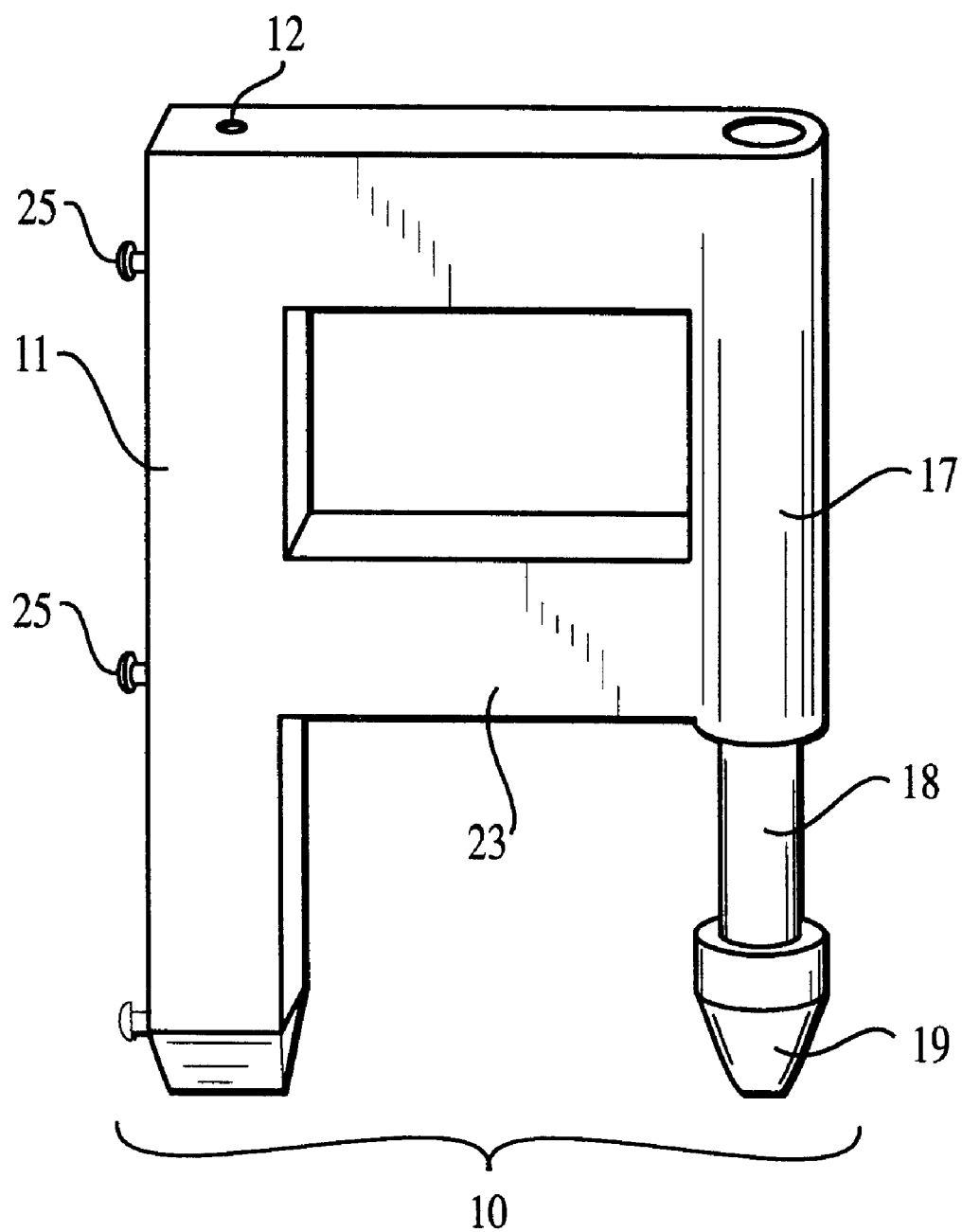
FIG. 1 is a perspective view showing a device for guiding a puncture needle according to a preferred embodiment of the invention wherein a pole brace is provided with a leg and a rubber support by which an amount of protrusion can be changed.

FIG. 1 through FIG. 6C are views each illustrating a device for guiding a puncture needle according to each preferred embodiment belonging to a first group of the present invention. FIG. 1 is a perspective view showing a device for guiding a puncture needle according to a preferred embodiment of the invention wherein a pole brace is provided with a leg and a rubber support by which an amount of protrusion can be changed.

The device 10 for guiding a puncture needle comprises a guide section 11 containing an insertion hole 12 for a needle, a pole brace 17 standing erect in substantially parallel to the guide section 11 and further provided with a leg 18 by which an amount of protrusion can be changed, and a beam (cross beam) 23 for connecting the guide section 11 to the pole brace 17. The leg 18 contains a support, for example, a rubber support 19 (hereinafter referred to as "rubber support", but it is to be noted that the support is not limited to rubber) for preventing slippage in case of fixing the guiding device 10 to the surface of a subject's body.

In order to make applicable for various uses, the guiding device may be constituted that the insertion hole 12 is defined rather large, several screws 25 for fixing an introducer 5 which will be mentioned hereinafter are disposed on a side of the guide section 11 as a fixing means for the introducer 5, whereby the introducer 5 is pressed and fixed due to clamping of fixing screws 25.

In the present embodiment, the beam 23 for connecting both the guide section 11 and the pole brace 17 may be prepared from, for example, a colorless clear acrylic plastic material into an integrally molded product in order to prevent from appearance of an image of the guiding device 10 in a pictorial image as a result of transmission through X-rays.

Figure 2:
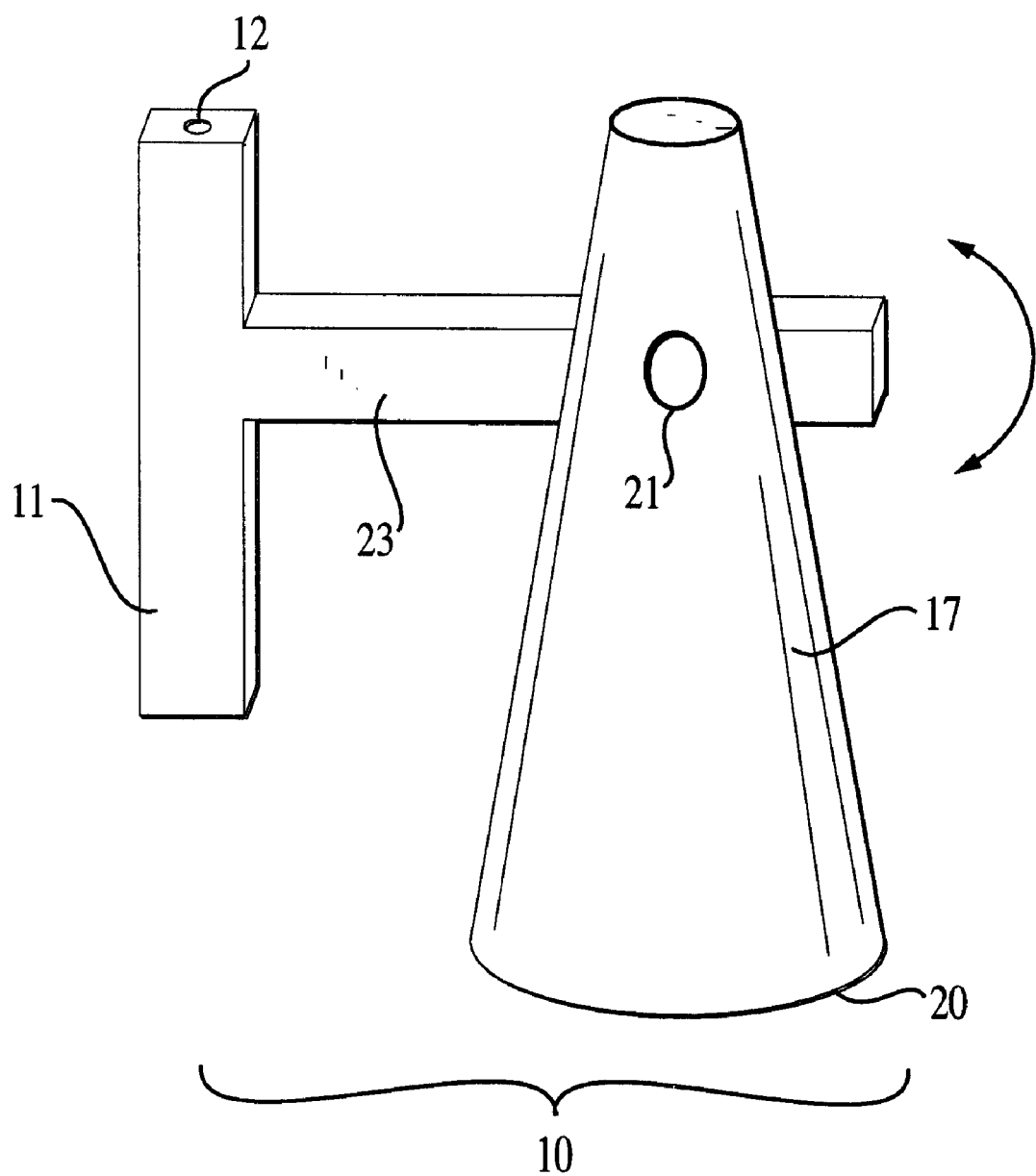
FIG. 2 is a perspective view showing a device for guiding a puncture needle according to another preferred embodiment of the invention wherein the bottom of a brace is formed into a conical non slip leg.

FIG. 2 is a perspective view showing a device for guiding a puncture needle according to another preferred embodiment of the invention wherein the bottom of a brace is formed into a conical nonslip leg.

The device 10 for guiding a puncture needle comprises a guide section 11 containing an insertion hole 12 for a needle, a pole brace 17 standing erect in substantially parallel to the guide section 11 and further provided with a conical nonslip leg 20 the bottom of which can assure a wide area for placing the guiding device 10 in case of fixing it on the surface of a subject s body, and a beam 23 for connecting the guide section 11 to the pole brace 17. The pole brace 17 is fixed to the beam 23 at a bearing 21 wherein an angle of support is adjustable.

In the present embodiment, the guide section 11 and the beam 23 may be prepared from, for example, a colorless clear acrylic plastic material into an integrally molded product.

Figure 3:
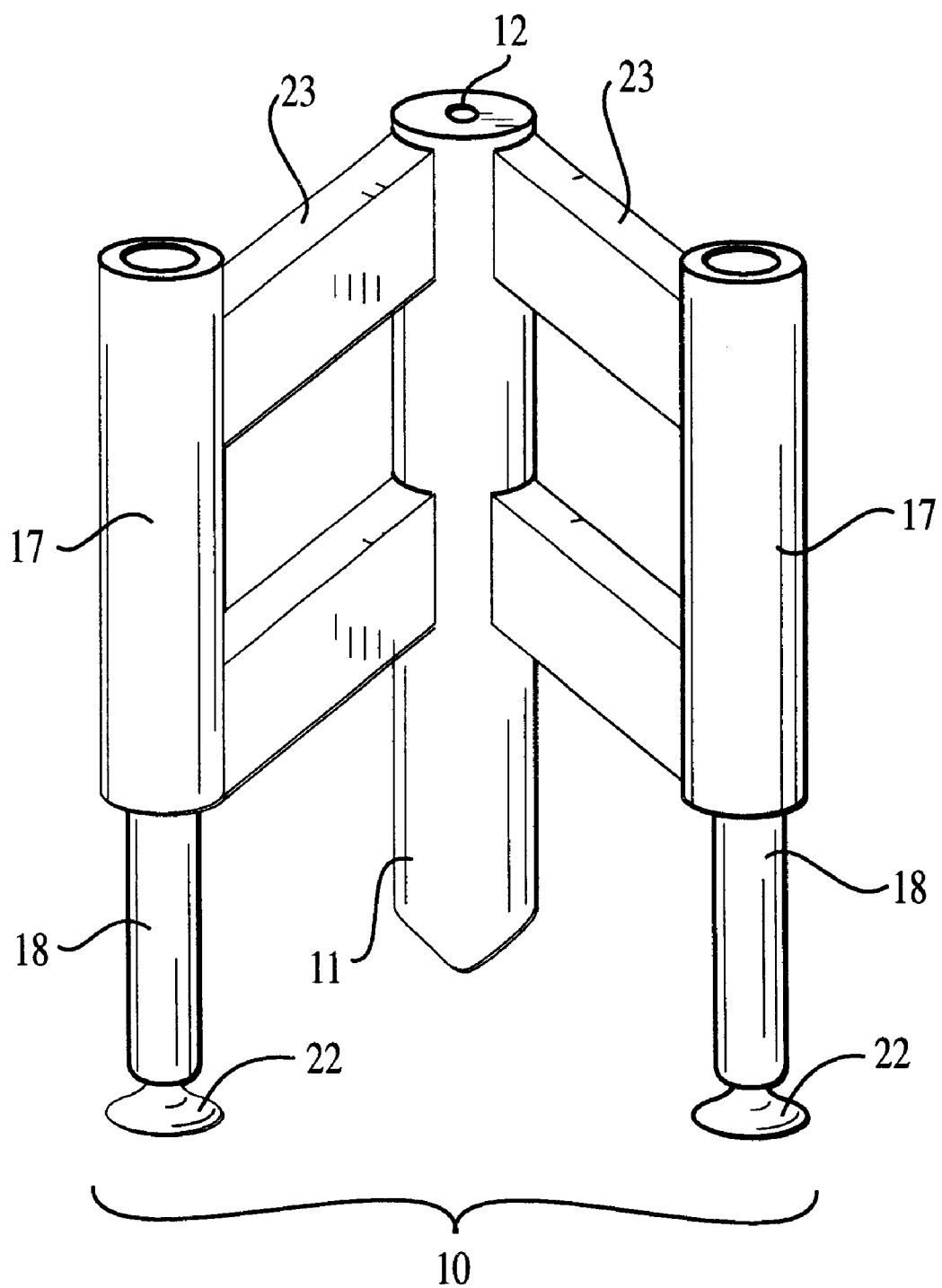
FIG. 3 is a perspective view showing a device for guiding a puncture needle according to a still another preferred embodiment of the invention wherein the device is provided with two pole braces.

FIG. 3 is a perspective view showing a device for guiding a puncture needle according to a still another preferred embodiment of the invention wherein the device is provided with two pole braces.

The device 10 for guiding a puncture needle comprises a guide section 11 containing an insertion hole 12 for a needle, two pole braces 17 each standing erect in substantially parallel to the guide section 11 and further provided with a leg 18 by which an amount of protrusion can be changed, and two beams 23 for integrally connecting two of the pole braces 17, and the guide section 11 in a triangular disposition.

Sucking disks 22 made of rubber or a plastic material each having sucking ability as a function for fixing the guiding device 10 to the surface of a subject's body are mounted to the legs 18, respectively.

In the present embodiment, two of the pole braces 17, and the guide section 11 disposed in a triangular form are connected integrally to each other, and these guide section 11, two of the pole braces 17; and two of the beams 23 may be prepared from, for example, a colorless clear acrylic plastic material into an integrally molded product.

Figure 4:
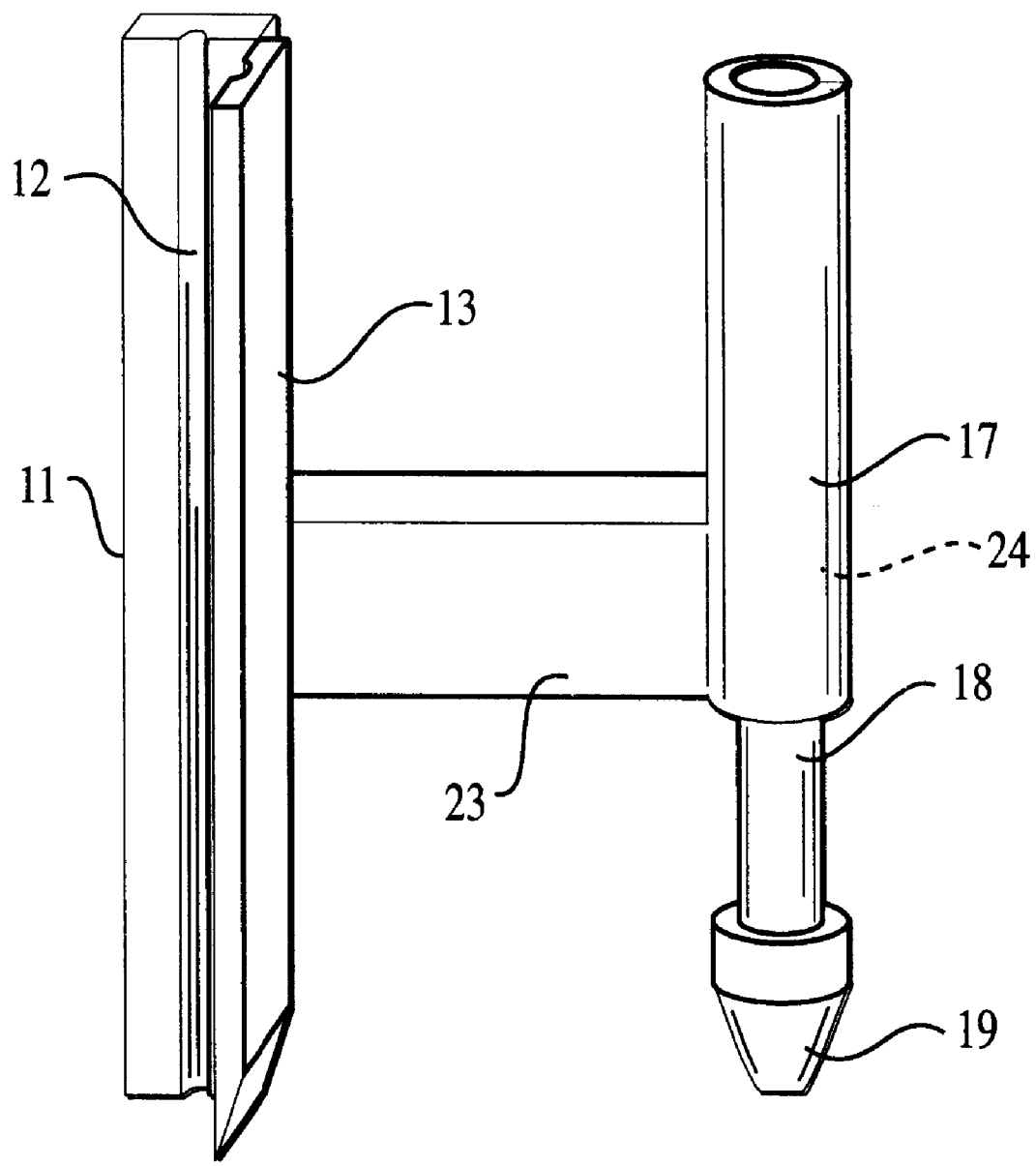
FIG. 4 is a perspective view showing a yet further preferred embodiment of the invention wherein a hinged holding section in a guide section is opened.

FIG. 4 is a perspective view showing a yet further preferred embodiment of the invention wherein a hinged holding section in a guide section is opened.

The device 10 for guiding a puncture needle comprises a guide section 11 containing an insertion hole 12 for a needle, a pole brace 17 standing erect in substantially parallel to the guide section 11 and further provided with a leg 18 by which an amount of protrusion for fixing the device to a subject's body surface can be changed, and a beam 23 for connecting the guide section 11 to the pole brace 17, In this case, a beam connecting section 24 for the pole brace 17 and the beam 23 may be constituted in such that the pole brace 17 (and the beam 23) can be rotated around the leg 18 as the axis, if necessary. The guide section 11 contains an openable hinged holding section 13 which is opened in a parallel state to the insertion hole 12 as a holding mechanism in order that the guiding device 10 can be attached to and detached from an introducer and a puncture needle in the longitudinal direction of the insertion hole 12, In case of closing the insertion hole 12, the hinge is closed to secure the hinged holding section 1a to the guide section 11 by means of a locking mechanism (not shown) or the like.

When the hinged holding section 1a is opened in the guide section 11, the insertion hole 12 is opened, whereby the introducer and the puncture needle which have been inserted in the insertion hole 12 can be easily attached and detached.

In the present embodiment, the guide section 11, the pole brace 17, and the beam 23 for connecting both these members to each other may be prepared from, for example, a colorless clear acrylic plastic material into an integrally molded product. The holding section 13 to be hinged with respect to the guide section 11 has been prepared by separately molding the same.

A rubber support 19 made of a rubber material and for preventing slippage in case of fixing the guiding device 10 to the surface of a subject's body is mounted to the leg 18. A projection which produces a shallow depression in the case when the guiding device 10 is placed on a subject's body surface may be defined on the bottom of the rubber support 19.

In each of the devices for guiding puncture needle in the preferred embodiments shown in FIGS, 1 through 4, a height of each guide section is constituted to be the same as that of each pole brace (including each leg) which stands erect in parallel to the guide section. If the guide section has the same height as that of the pole brace, then insertion, attachment or detachment of an introducer and a puncture needle into an insertion hole become easy in case of employing the guiding device, Furthermore, manipulation by an examiner is easily performed through a subject's body surface.

Figure 5:
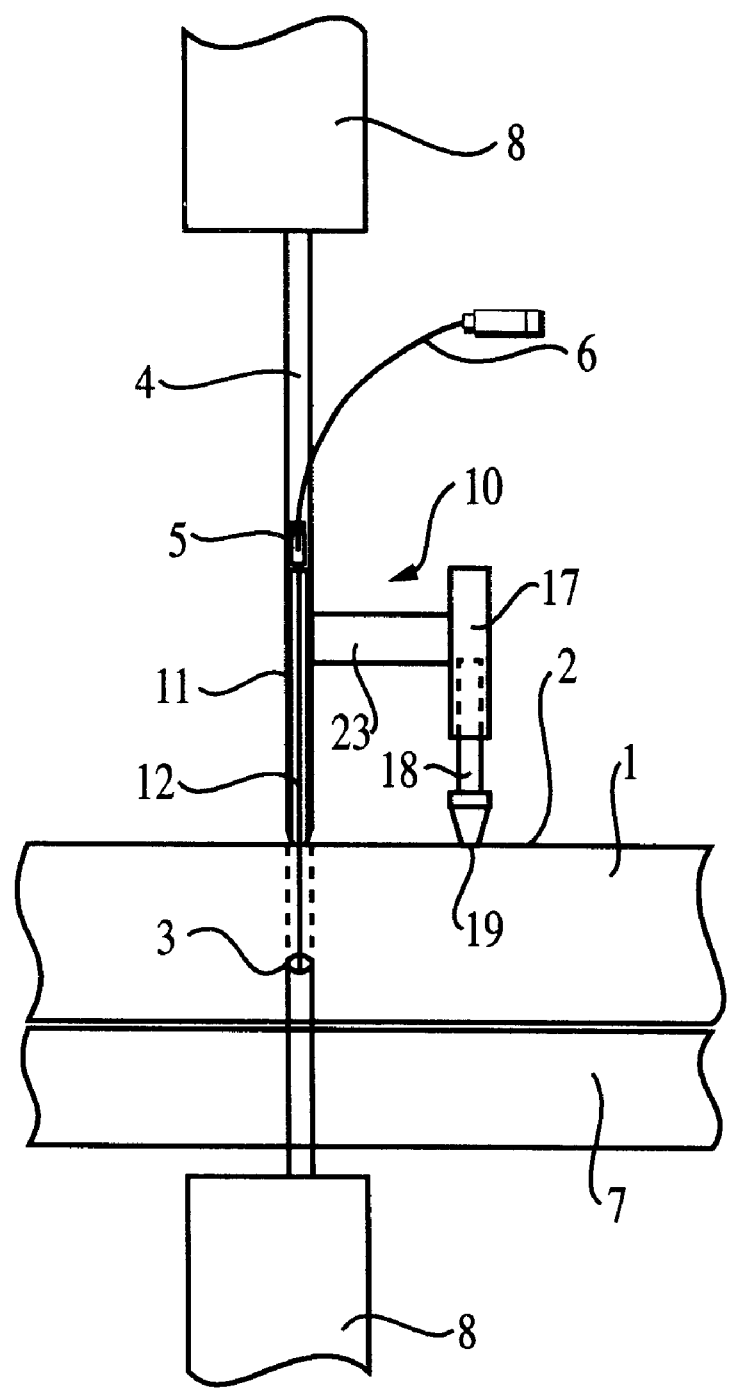
FIG. 5 is an explanatory view showing a situation wherein a device for guiding a puncture needle according to the present invention is applied to a subject.

FIG. 5 is an explanatory view showing a situation wherein a device for guiding a puncture needle according to the present invention is applied to a subject.

In order to obtain image data of laminar plane (sliced plane, scanned plane) by a CT apparatus, a subject 1 is laid on a table 7 in the CT apparatus. A needle is pierced percutaneously towards a target site 3 by an examiner (not shown) through a cuticle 2 on the pectoral region or the abdominal parts of the subject 1. A device 10 for guiding a puncture needle is used for puncturing exactly and percutaneously the target site 3.

A device 10 for guiding a puncture needle (included in the devices for guiding puncture needle in the embodiments belonging to the first group shown in FIGS. 1 to 4) is placed on the cuticle 2 in the pectoral region or the abdominal part of the subject 1 positioned in an X-radiation section 4 of a gantry 8. A target site is confirmed by the examiner, then, the examiner decides a position, depth, and direction (puncturing route) for puncturing with a needle, and the device 10 for guiding a puncture needle is secured to be aligned with a puncturing line, Without any delay, the examiner punctures the cuticle 2 with the needle so as to exactly reach the target site 3 while confirming the needle-point of the puncture needle in accordance with an image determined, and in this case, the puncturing operation is carried out while maintaining the needle in parallel to a cross section of CT image.

In case of puncturing with a needle by the use of the device for guiding a puncture needle, there are a case wherein first, the introducer 5 is positioned on the cuticle 2, and a case wherein puncturing is made shallow with respect to the cuticle 2. Then, the puncture needle 6 is pierced towards the target site 3 through the introducer 5. In these circumstances, the examiner practices predetermined manipulation such as infusion of a medicine, and biopsy through the puncture needle 6 thus pierced. In this case, the examiner is especially required to be accorded with the puncturing route determined in an image, and exact piercing can be made with respect to a target site, when a device for guiding a puncture needle according to a preferred embodiment of the invention is utilized.

Figure 6C:
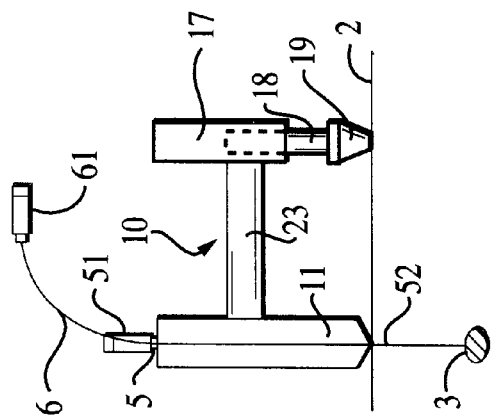
FIG. 6C shows a procedural stage when a puncture needle has pierced the target site.
Figure 6B:
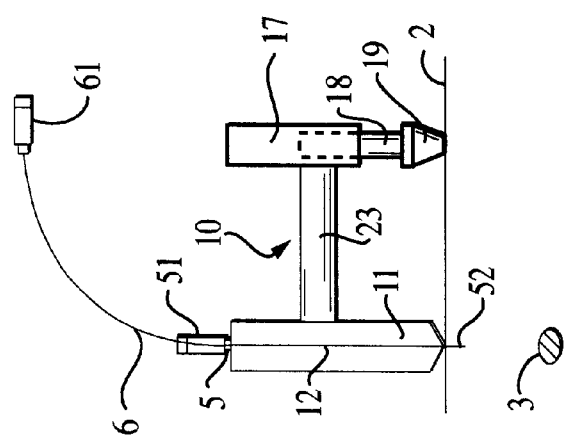
FIG. 6B shows a procedural stage when a puncture needle is inserted into the introducer.
Figure 6A:
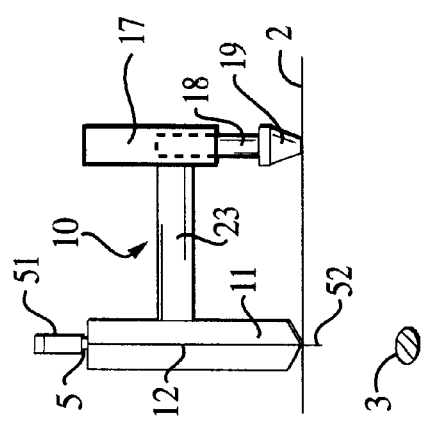
FIG. 6A shows a procedural stage when an introducer is inserted.

FIGS. 6A, 6B, and 6C are explanatory views each showing procedure steps 1 to 5 in case of using a device for guiding a puncture needle according to preferred embodiments of the present invention. It is to be noted herein that a CT image is accorded to a target determined by manipulation for puncturing with a needle obtained in real time image under CT transmission.

FIG. 6A is an explanatory view showing a situation wherein the introducer 5 is fitted to the insertion hole 12 of the guide section 11, and a needlepoint 52 of the introducer 5 is set to a puncturing point of the cuticle 2.

Procedure Step 1: An examiner confirms the target site 3 under real time CT transmission, and decides a puncturing point and a puncturing route.

Procedure Step 2: The introducer 5 has been previously set to the guide section 11, and the needlepoint 52 of the introducer 5 is aligned to the puncturing point. A height of the pole brace 17 is adjusted so as to be in parallel to a CT laminar plane and adapted to be the puncturing route by employing a function for varying an amount of projection in the leg 18 of the pole brace 17. (In case of FIG. 2, adjustment of direction is carried out by utilizing a rotating function centering around the bearing 21, In case of FIG. 4, the guiding device 102,S secured to the surface of the subject's body 1 by the use of functions in the sucking disk 22.) It is to be noted that the pole brace 17 is set so as to inevitably deviate from the X-radiation section 4.

Procedure Step 3: An examiner confirms the puncturing route to puncture lightly a subject's cuticle with the needlepoint 52 of the introducer 5 (in case of puncturing).

FIG. 6B is an explanatory view showing a situation wherein the introducer 5 into which the puncture needle 6 has been inserted is directed to the target site 3, Procedure Step 4: A needle base 61 of the puncture needle 6 is held, and the puncture needle 6 is inserted in a curved state wherein elasticity of the puncture needle 6 is utilized from a needle base 51 of the introducer 5 at a position where the x-radiation section 4 is avoided.

FIG. 6C is an explanatory view showing a situation in the case where the puncture needle 6 is directed to pierce a target site 3.

Procedure Step 5: The puncture needle 6 is pierced into the target site 3 while observing an image under CT transmission. After it could be confirmed that the needlepoint 62 of the puncture needle 6 resided in the target site 3, a predetermined manipulation such as infusion of a medicine, and biopsy is carried out.

In this case, if it is required to remove the guiding device 10 from the subject's body surface, the hinged holding section 13 is opened to leave the introducer 5 and the puncture needle 6 in their pierced state, and the introducer 5 and the puncture needle 6 are released from the insertion hole 12 of the guide section 11, whereby the guiding device 10 can be removed from the subject's body surface.

PREFERRED EMBODIMENTS IN SECOND GROUND

FIGS. 7 through 12C are views showing devices for guiding puncture needle according to preferred embodiments of the invention belonging to a second group.

Figure 7:
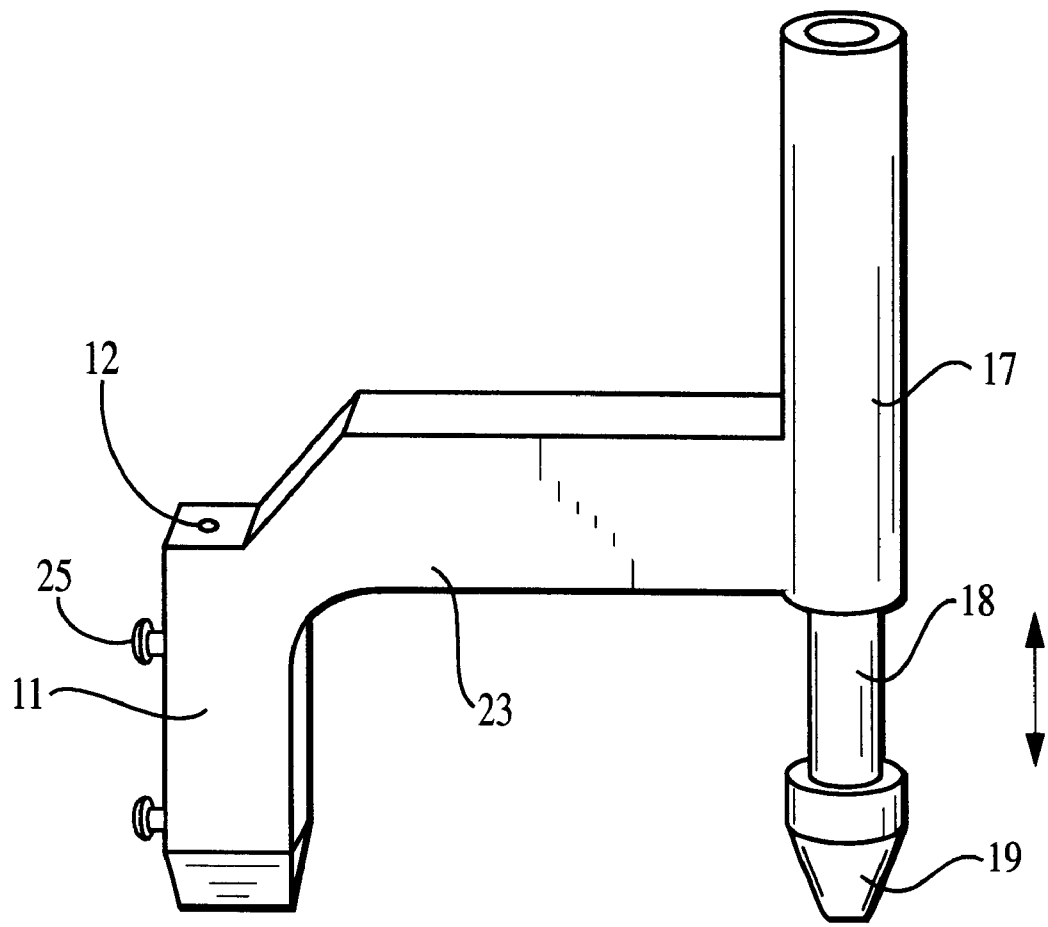
FIG. 7 is a perspective view showing a device for guiding a puncture needle according to a preferred embodiment of the invention wherein a pole brace is provided with a leg and a rubber support by which an amount of protrusion can be changed.

FIG. 7 is a perspective view showing a device for guiding a puncture needle according to a preferred embodiment of the invention wherein a pole brace is provided with a leg and a rubber support by which an amount of protrusion can be changed.

The device 10 for guiding a puncture needle comprises a short guide section 11 containing an insertion hole 12 for a needle, a pole brace 17 standing erect in substantially parallel to the guide section 11 and further provided with a leg 18 by which an amount. of protrusion can be changed, and a beam 23 for connecting integrally the guide section 11 to the pole brace 17, In this case, the guide section 11 extends downwards from a connecting section formed with the beam 23.

The leg 18 contains a support, for example, a rubber support 19 (hereinafter referred to as "rubber support", but it is to be noted that the support is not limited to rubber) for preventing slippage in case of fixing the guiding device 10 to the surface of a subject's body.

In order to make applicable for various uses, the guiding device may be constituted in such that the insertion hole 12 is defined rather large, several screws 25 for fixing an introducer 5 which will be mentioned hereinafter are disposed on a side of the guide section 11 as a fixing means for the introducer 5, whereby the introducer 5 is pressed and fixed due to clamping of fixing screws 25.

In the present embodiment, the beam 23 for connecting both the short guide section 11 and the pole brace 17 may be prepared from, for example, a colorless clear acrylic plastic material into an integrally molded product in order to prevent from appearance of an image of the guiding device 10 in a pictorial image as a result of transmission through X-rays.

Figure 8:
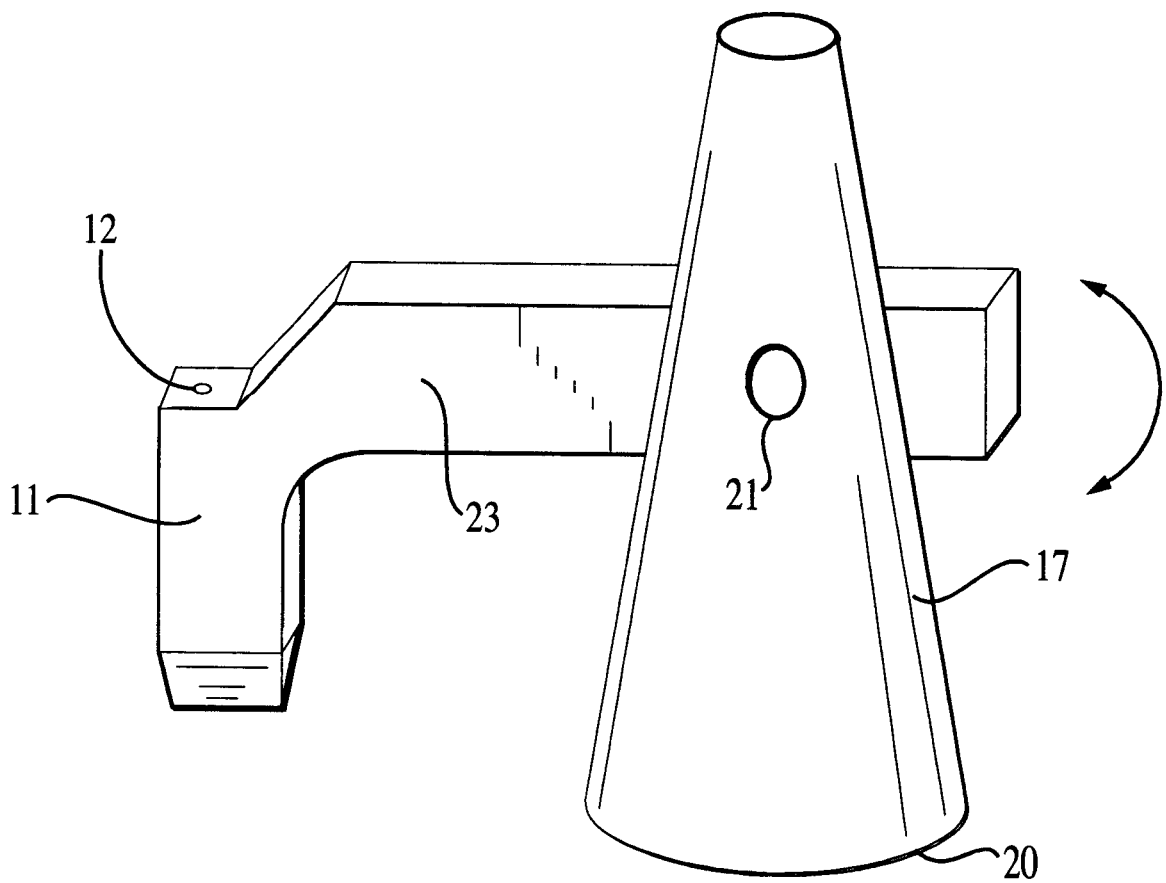
FIG. 8 is a perspective view showing a device for guiding a puncture needle according to another preferred embodiment of the invention where in the bottom of a brace is formed into a conical nonslip leg.

FIG. 8 is a perspective view showing a device for guiding a puncture needle according to another preferred embodiment of the invention wherein the bottom of a brace is formed into a conical nonslip leg.

The device 10 for guiding a puncture needle comprises a short guide section 11 containing an insertion hole 12 for a needle, a pole brace 17 standing erect in substantially parallel to the guide section 11 and further provided with a conical nonslip leg 20 the bottom of which can assure a wide area for placing the guiding device 10 in case of fixing it on the surface of a subject's body, and a beam 23 for connecting the guide section 11 to the pole brace 17. The pole brace 17 is fixed to the beam 23 at a bearing 21 wherein an angle of support is adjustable.

In the present embodiment, the short guide section 11 and the beam 23 m ay be prepared from, for example, a colorless clear acrylic plastic material into an integrally molded product.

Figure 9:
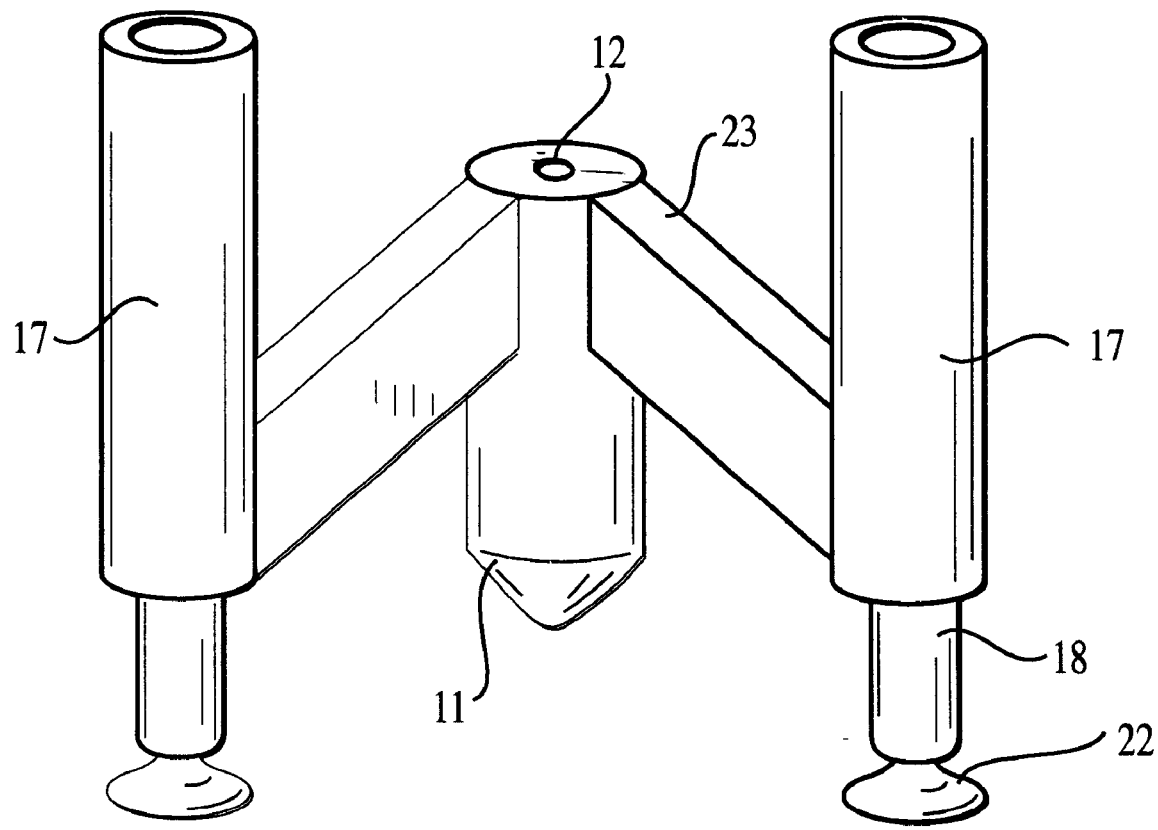
FIG. 9 is a perspective view showing a device for guiding a puncture needle according to a still another-preferred embodiment of the invention wherein the device is provided with two pole braces.

FIG. 9 is a perspective view showing a device for guiding a puncture needle according to a still another preferred embodiment of the invention wherein the device is provided with two pole braces.

The device 10 for guiding a puncture needle comprises a short guide section 11 containing an insertion hole 12 for a needle, two pole braces 17 each standing erect in substantially parallel to the guide section 11 and further provided with a leg 18 by which an amount of protrusion can be changed, and two beams 23 for integrally connecting two of the pole braces 17, and the guide section 11 in a triangular disposition.

Sucking disks 22 made of rubber or a plastic material each having sucking ability as a function for fixing the guiding device 10 to the surface of a subject's body are mounted to the legs 18, respectively.

In the present embodiment, two of the pole braces 17, and the short guide section 11 disposed in a triangular form are connected integrally to each other, and these guide section 11, two of the pole braces 17, and two of the beams 23 may be prepared from, for example, a colorless clear acrylic plastic material into an integrally molded product.

Figure 10:
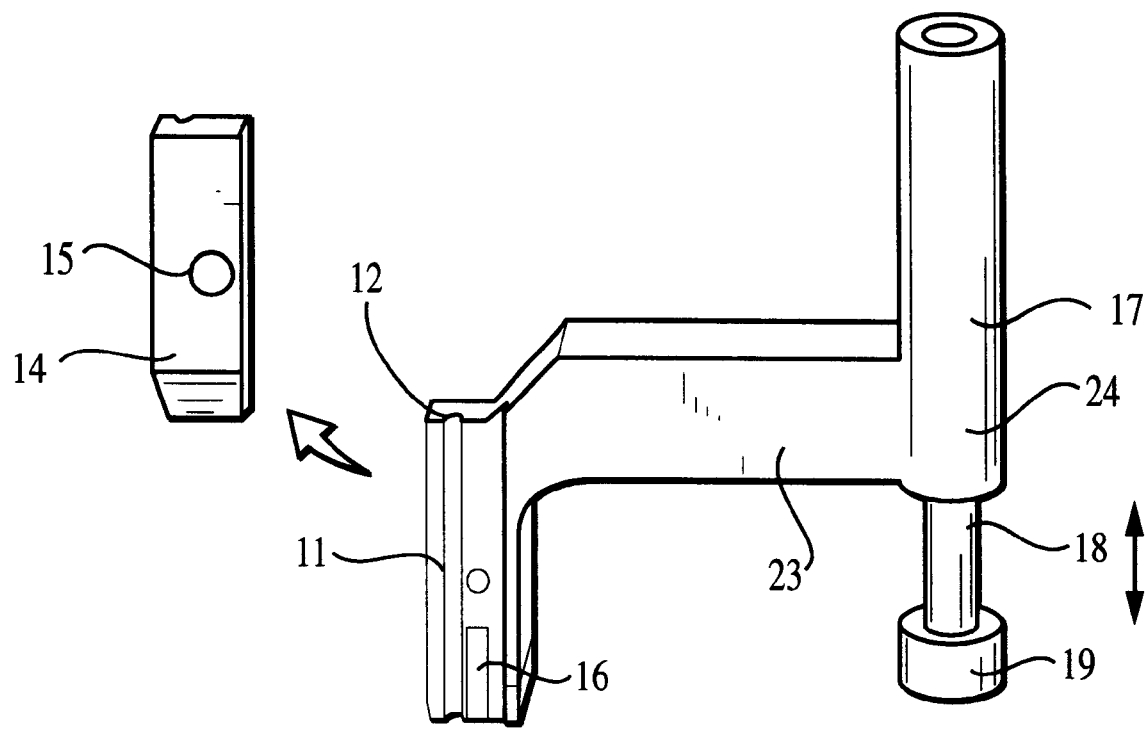
FIG. 10 is a perspective view showing a yet further preferred embodiment of the invention wherein a detachable holding section mounted on a guide section is detached.

FIG. 10 is a perspective view showing a yet further preferred embodiment of the invention wherein a detachable holding section in a guide section is opened.

The device 10 for guiding a puncture needle comprises a short guide section 11 containing an insertion hole 12 for a needle, a pole brace 17 standing erect in substantially parallel to the guide section 11 and further provided with a leg 18 by which an amount of protrusion for fixing the device to a subject's body surface can be changed, and a beam 23 for connecting integrally the guide section 11 to the pole brace 17. In this case, a beam connecting section 24 for the pole brace 17 and the beam 23 may be constituted in such that the pole brace 17 (and the beam 23) can be rotated around the leg 18 as the axis, if necessary. The guide section 11 contains a detachable holding section 14 which is opened in a parallel state to the insertion hole 12 as a holding mechanism in order that the guiding device 10 can be attached to and detached from an introducer and a puncture needle in the longitudinal direction of the insertion hole 12. In case of closing the insertion hole 12, the holding section 14 is secured to the guide section 11 by means of a locking screw.

When the holding section 14 is removed from the guide section 11 to open the insertion hole 12, whereby-the introducer and the puncture needle which have been inserted in the insertion hole 12 can be released therefrom.

In the present embodiment, the guide section 11, the pole brace 17, and the beam 23 for connecting both these members to each other may be prepared from, for example, a colorless clear acrylic plastic material into an integrally molded product, The detachable holding section 14 has been prepared by separately molding the same.

A rubber support 19 made of a rubber material and for preventing slippage in case of fixing the guiding device 10 to the surface of a subject's body is mounted to the leg 18. A projection which produces a shallow depression in the case when the guiding device 10 is placed on a subject's body surface may be defined on the bottom of the rubber support 19.

Thin metal plates or sheets 16 (or a metallic thin wire) have been mounted to the guide section 11 according to the preferred embodiment shown in FIG. 10. The image of the plates generated by applying radiation from the gantry are displayed as artifacts (lines serving as indices of puncturing route) in a display. For instance, if the metal plate 16 having about 0.1 mm thickness has been mounted to the guide section 11, a dark line corresponding to the metallic thin sheet 16 appears when the guiding device is subjected to X-radiation. Accordingly, it can be confirmed whether or not a guiding device is exactly-set on a sliced plane of a puncture link. It is desired to use a metallic thin sheet 16 (or a metallic thin wire) producing a black line of around 0.1 mm in its image which can be recognized by an examiner. When the metal plate 16 is disposed at a position close to the insertion hole 12 it becomes possible to assure higher precision in alignment of the insertion hole 12 with a puncture line.

In each of the devices for guiding puncture needle according to the preferred embodiments shown in FIGS. 7 through 10, it is constituted such that a height of a guide section is lower than that of a pole brace (including a leg) standing erect in parallel to the guide section. When a height of the guide section is lower than that of the pole brace, a distance in space defined between an area extending under the gantry of a CT apparatus and a subject's 1 body surface can be maintained widely in case of employing a guiding device, so that this arrangement brings about a characteristic feature that a visual field becomes wider for an examiner, whereby observation upon a subject's body surface and manipulation by the examiner becomes easier.

Figure 11:
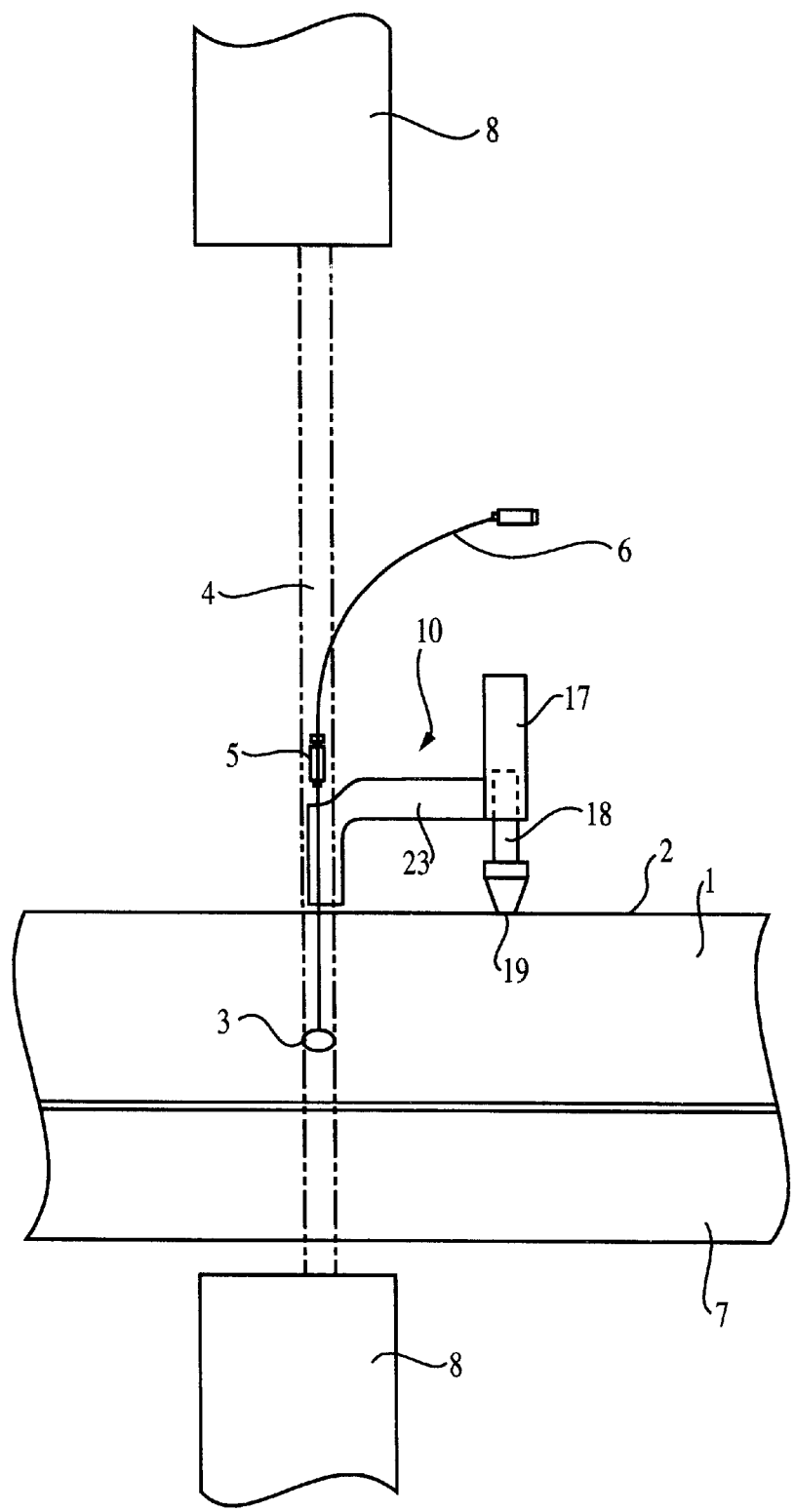
FIG. 11 is an explanatory view showing a situation wherein a device for guiding a puncture needle according to the present invention is applied to a subject.

FIG. 11 is an explanatory view showing a situation wherein a device for guiding a puncture needle according to the present invention is applied to a subject.

In order to obtain image data of laminar plane (sliced plane, scanned plane) by a CT apparatus, a subject 1 is laid on a table 7 in the CT apparatus. A needle is pierced percutaneously towards a target site 3 by an examiner (not shown) through a acuticle 2 on the pectoral region or the abdominal part of the subject 1. A device 10 for guiding a puncture needle is used for puncturing exactly and percutaneously the target site 3.

A device 10 for guiding a puncture needle (included in the devices for guiding puncture needle in the embodiments belonging to the second group shown in FIGS. 7 to 10) is placed on the cuticle 2 in the pectoral region or the abdominal part of the subject 1 positioned in an X-radiation section 4 of a gantry 8. A target site is confirmed by the examiner, then the examiner decides a position, depth, and direction (puncturing route) for puncturing with a needle and the device 10 for guiding a puncture needles secured to be aligned with a puncturing line. Without any delay, the examiner punctures the cuticle 2 with the needle so as to exactly reach the target site 3 while confirming the needle-point of the puncture needle in accordance with an image determined, and in this case, the puncturing operation is carried out while maintaining the needle in parallel to a cross section of CT image.

In case of puncture with a needle by the use of the device for guiding a puncture needle, there are a case wherein first, the introducer 5 is positioned on the cuticle 2, and a case wherein puncturing is made shallow with respect to the cuticle 2.

Then, the puncture needle 6 is pierced towards the target site 3 through the introducer 5. In these circumstances, the examiner practices predetermined manipulation such as infusion of a medicine, and biopsy through the puncture needle 6 thus pierced. In this case the examiner is especially required to be accorded with the puncturing route determined in an image, and exact piercing can be made with respect to a target site, when a device for guiding a puncture needle according to a preferred embodiment of the invention is utilized.

Figure 12C:
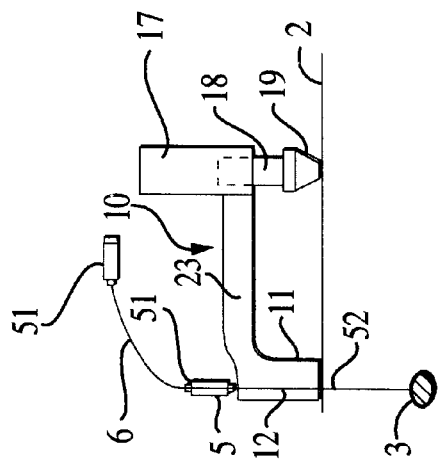
FIG. 12C shows a procedural stage when a puncture needle has pierced the target site.
Figure 12B:
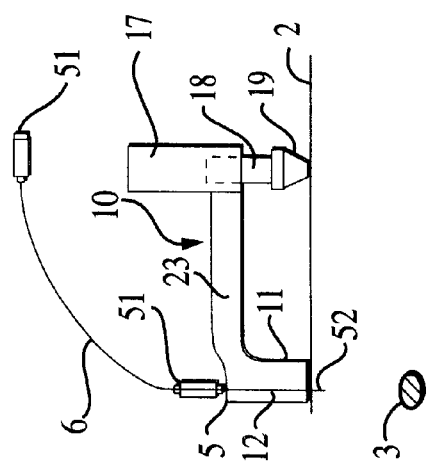
FIG. 12B shows a procedural stage when a puncture needle is inserted into an introducer.
Figure 12A:
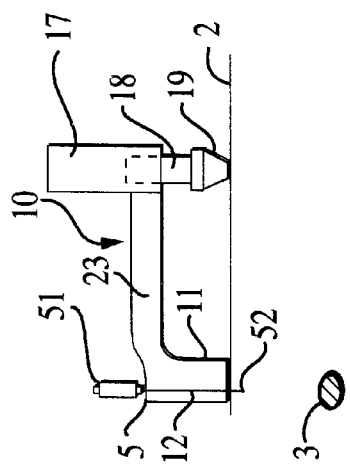
FIGS. 12A shows a procedural stage when an introducer is inserted into an insertion hole.

FIGS. 12A, 12B, and 12C are explanatory views each showing procedure steps 1 to 5 in case of using a device for guiding a puncture needle according to preferred embodiments of the present invention4 It is to be noted herein that a CT image is accorded to a target determined by manipulation for puncturing with a needle obtained in real time image under CT transmission.

FIG. 12A is an explanatory view showing a situation wherein the introducer 5 is fitted to the insertion hole 12 of the guide section 11, and a needlepoint 52 of the introducer 5 is set to a puncturing point of the cuticle 21.

Procedure Step 1: An examiner confirms the target site 3 under real time CT transmission, and decides a puncturing point and a puncturing route.

Procedure Step 2: The introducer 5 has been previously set to the guide section lit and the needlepoint 52 of the introducer 5 is aligned to the puncturing point. A height of the pole brace 17 is adjusted so as to be in parallel to a CT laminar plane and adapted to be the puncturing route by changing suitably an amount of projection in the leg 18 of the pole brace 17. (In case of FIG. 8, adjustment of direction is carried out by utilizing a rotating function centering around the bearing 21. In case of FIG. 9, the guiding device 10 is secured to the surface of the subject's body 1 by the use of functions in the suction disk 22.) It is to be noted that the pole brace 17 is set so as to inevitably deviate from the X-radiation section 4.

Procedure Step 3: An examiner confirms the puncturing route to puncture lightly a subject's cuticle with the needlepoint 52 of the introducer 5 (in case of puncturing).

FIG. 12B is an explanatory view showing a situation wherein the introducer 5 into which the puncture needle 6 has been inserted is directed to the target site 3.

Procedure Step 4: A needle base 61 of the puncture needle 6 is held; and the puncture needle 6 is inserted in a curved state wherein elasticity of the puncture needle 6 is utilized from a needle base 51 of the introducer 5 at a position where the X-radiation section 4 is avoided.

FIG. 12C is an explanatory view showing a situation in the case where the puncture needle 6 is directed to pierce a target site 3.

Procedure Step 5: The puncture needle 6 is pierced into the target site 3 while observing an image under CT transmission. After it could be confirmed that the needlepoint 62 of the puncture needle 6 resided in the target site 3, a predetermined manipulation such as infusion of a medicine, and biopsy is carried out.

In this case, if it is required to remove the guiding device 10 from the subject's body surface, the holding section 14 is removed (the insertion hole 12 is opened) by releasing the locking screw is to leave the introducer 5 and the puncture needle 6 in their pierced state, and the introducer 5 and the puncture needle 6 are released from the insertion hole 12 of the guide section 11; whereby the guiding device 10 can be removed from the subject's body surface.

In preferred embodiments according to the present invention, an adjustment is made in accordance with any of the following operations or the combination thereof before utilizing a device for guiding a puncture needle.

1. The needlepoint of an introducer which has been previously set in a guide section is aligned to a puncturing position in accordance with the puncturing position and a puncturing route which have been determined in a CT transmission image.
2. In order to conform to a laminar plane (a sliced plane, scanned plane) in CT, an amount of projection in a leg extending from a pole brace, rotation of a movable section or the like is adjusted.
3. In order to determine an angle based on which a puncture needle can reach a target position along a presupposed puncturing route, a whole guiding device is inclined laterally within a range of the laminar plane.

According to the above-mentioned operations 1–3 for positioning the guiding device, an exact puncturing route can be determined.

In preferred embodiments of the present invention, an insertion hole in a guide section has an inside diameter wherein an introducer and a puncture needle can be positively held in the case where the introducer is inserted in the insertion hole, and then the puncture needle is inserted in the introducer, besides the insertion hole must have a diameter into which the introducer can be inserted. In order to make a guiding device of the invention applicable for more various use applications it may be constituted in such that the insertion hole is defined slightly larger, several screws are positioned on a side of the guide section as a fixing means of the introducer, and the introducer is pressed by clamping these screws to secure the introducer.

According to the guiding device of a preferred embodiment of the invention, since an introducer is utilized for insertion of a puncture needle, a puncturing direction in the puncture needle is restricted, and since the puncture needle is protected by the introducer, it becomes possible to perform exact puncture with respect to a target site, so that it becomes possible to reduce a curvature of the needle during puncturing operation, even if a thin needle tube is used. Furthermore, even when the needle tube is inserted in a curved state, examiner's manipulation is carried out by holding directly a needle base of the puncture needle by the examiner, there is a peculiar advantage in that feeling of a needlepoint of the puncture needle can be sensed directly by examiner's fingertips. Moreover, since a puncture needle goes straight in accordance with a straight introducer after having been inserted in the introducer even if the puncture needle has been curved before inserting it into the introducer, there is no problem due to curvature of a needle tube for the puncture needle, Accordingly, higher precision in puncturing operation can be assured.

In a preferred embodiment of the present invention, since manipulation wherein a curved puncture needle is applied by the use of an introducer relates to an operation which deviates from an X-radiation section of a gantry, it is not required to lake a subject in and out from the gantry in every occasion of photographing, even if a distance extending from a lower end section to a subject's body surface is short, Thus, it becomes possible to avoid exposure to radiation upon examiner's hands, even in the manipulation under real time CT transmission.

When the device for guiding a puncture needle according to a preferred embodiment of the invention is used, a direction is determined with respect to a target site in accordance with an CT image, an introducer which defines an insertion route of-a puncture needle is inserted into an insertion hole in a guide section, the puncture needle pierces shallowly a subject's body surface, and then the puncture needle is inserted into the subject's body, so that such insertion of the puncture needle is easy. Accordingly, it becomes possible to apply such puncturing method that when a puncture needle is inserted from a needle base of an introducer within a gantry, the puncture needle in a curved state is inserted into an insertion hole of the needle base of the introducer within the gantry at a position deviating from an X-radiation section in the gantry by utilizing elasticity of a needle tube without any exposure to radiation upon an examiner and the examiner carries on insertion of the needle to puncture the target site.

Figure 13:
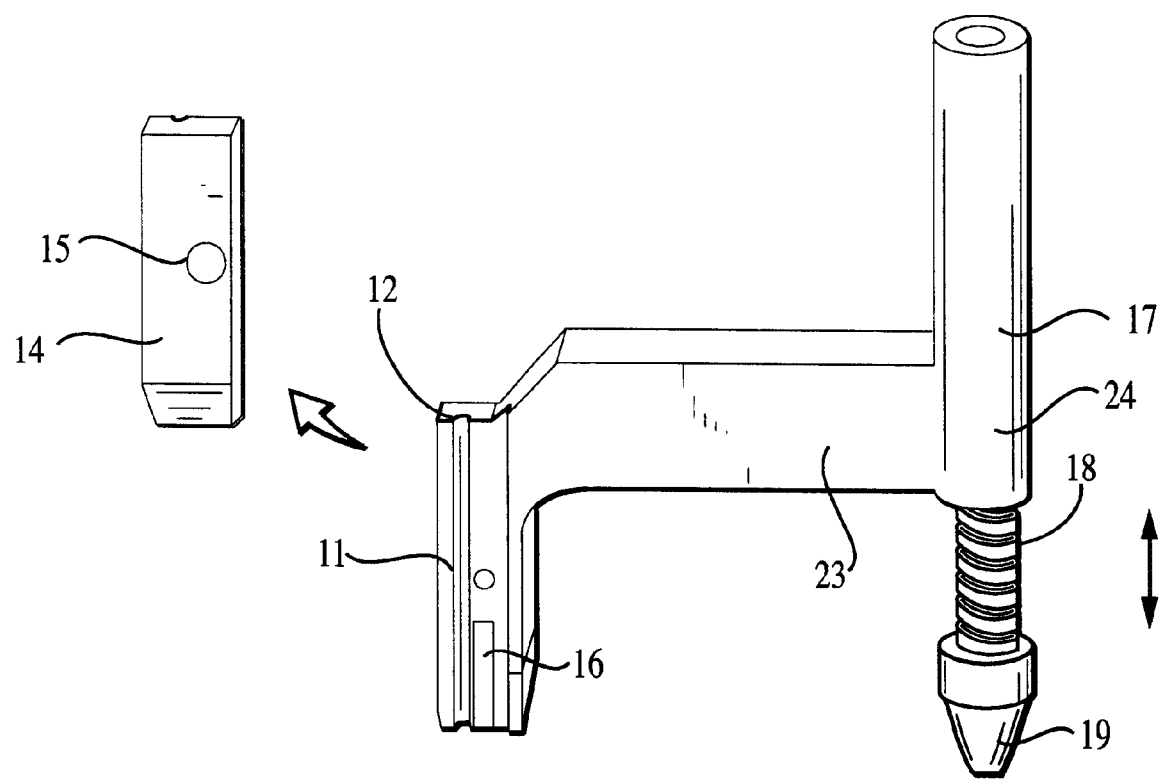
FIG. 13 is a perspective view showing a structure in the preferred embodiment of FIG. 10 wherein the leg section has been threaded.

FIG. 13 shows a structure wherein a leg 18 is threaded whereby an amount of projection is allowed to be variable, and the other part of the structure is common to that of FIG. 10.

Figure 14:
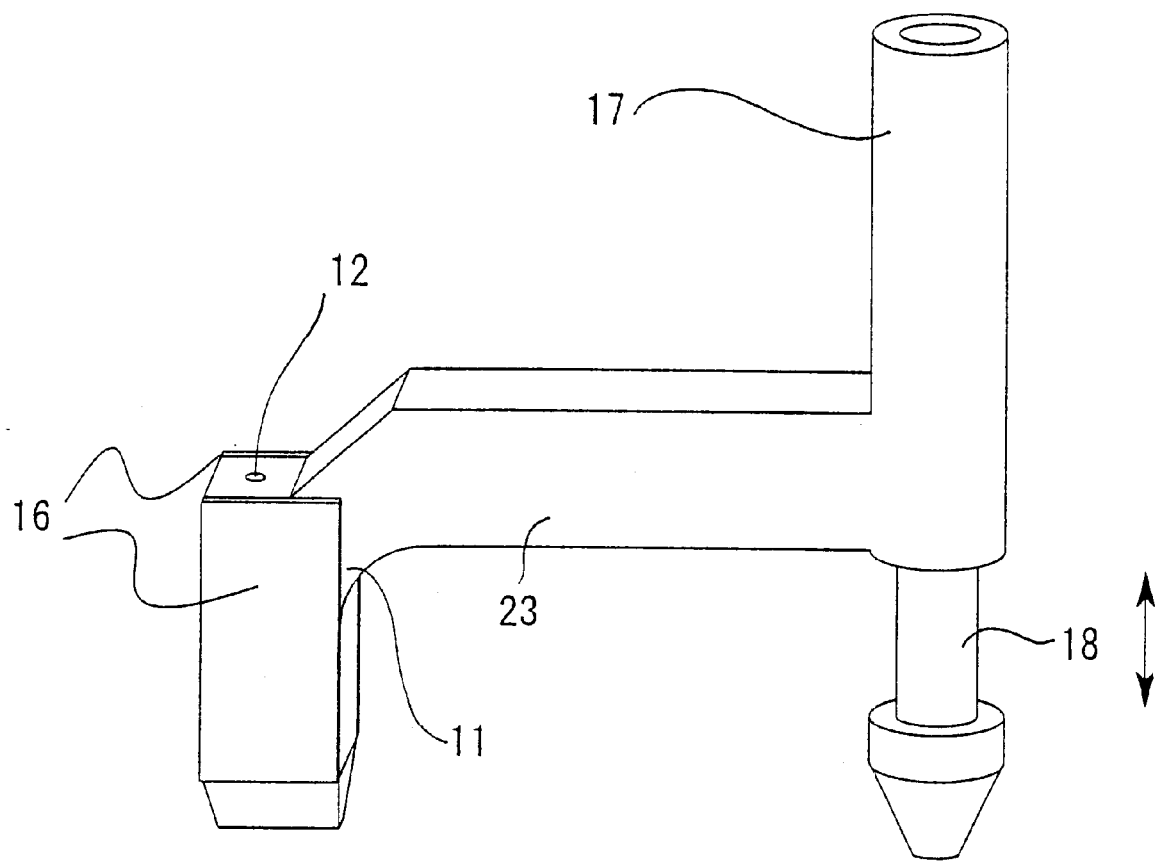
FIG. 14 is a perspective view showing a device for guiding a puncture needle according to a preferred embodiment of the invention wherein metal plates are provided for creating artifacts and the pole brace is variable in length.

FIG. 14 is a perspective view showing a device for guiding a puncture needle according to a preferred embodiment of the invention wherein a pole brace 17 is provided with a leg and a rubber support 18 by which an amount of protrusion can be changed.

The device is of similar form to the embodiment of FIG. 7 however, metal plates 16 are on either side of the short guide section 11. The metal plates 16 are parallel to each other, and opposite each other on the short guide section 11.

Figure 15:
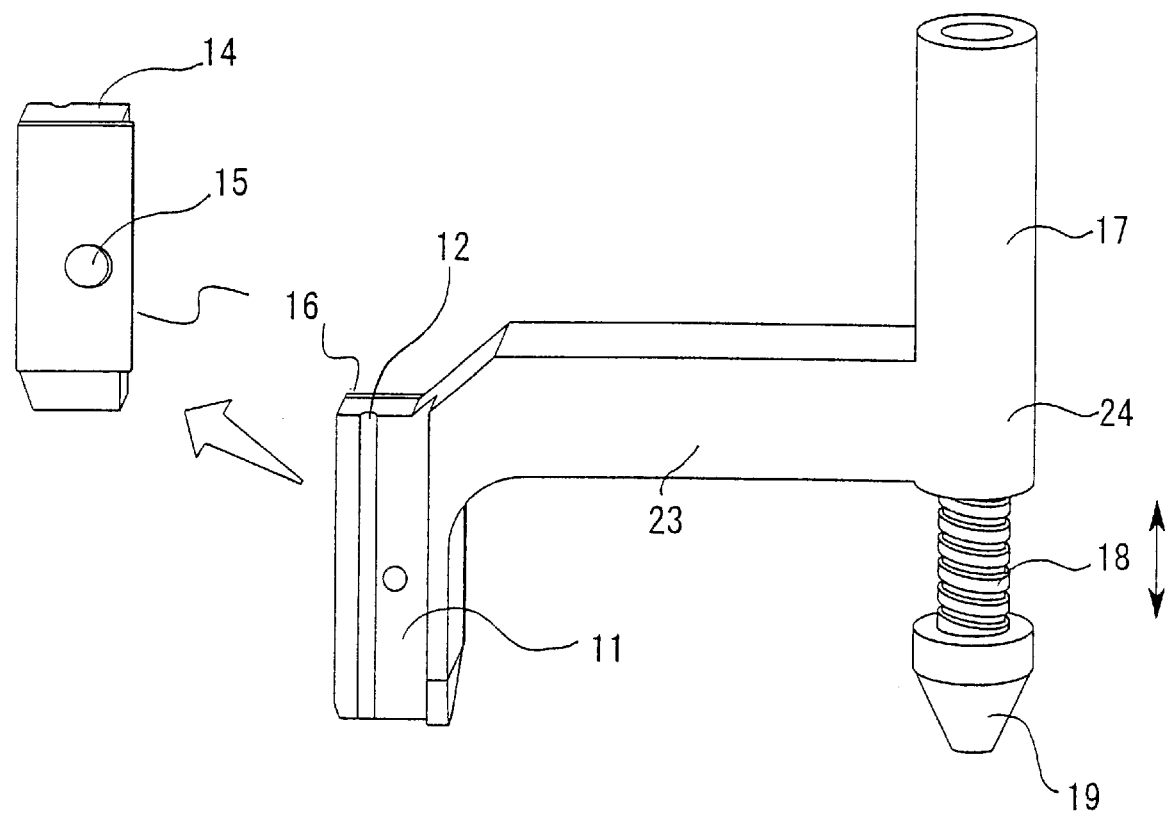
FIG. 15 is a perspective view showing a structure in the preferred embodiment of FIG. 13 wherein the guide section has metal plates for creating artifacts.

FIG. 15 is a perspective view showing a further preferred embodiment of the invention wherein a detachable holding section 14 in a guide section 11 is open. This embodiment is similar to that shown in FIG. 10 except here the metal plate 16 is found on the guide section 11 and the detachable holding section 14.

Figure 16:
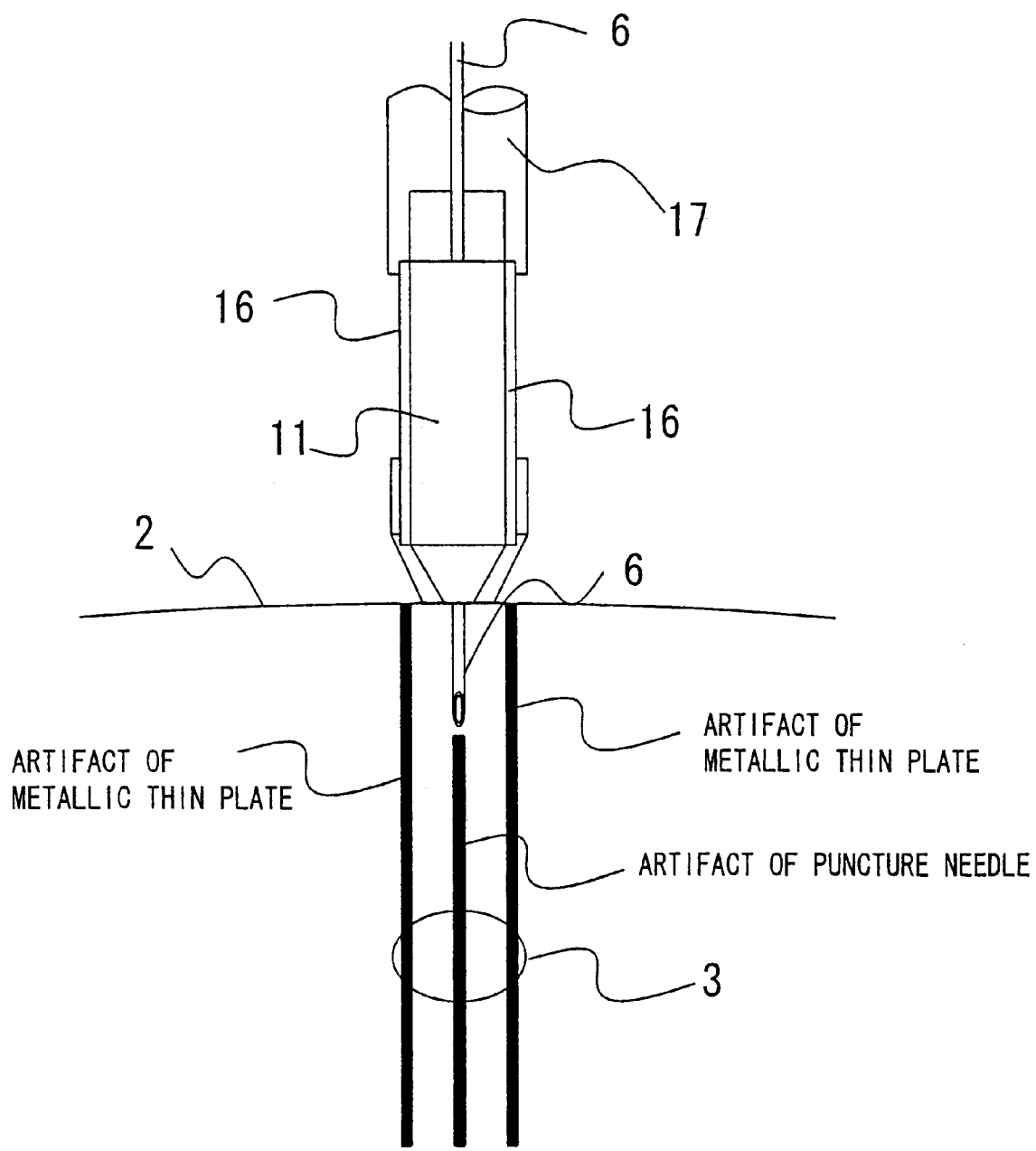
FIG. 16 is an explanatory view showing a situation wherein a device for guiding a puncture needle according to the present invention is applied to a subject.

FIG. 16 is an explanatory view showing a situation wherein a device for guiding a puncture needle according to the present invention is applied to a subject.

Two thin metal plates 16 are provided in parallel and opposite each other on the guide section 11, such that the guide section 11 is sandwiched by the metal plates 16. The metal plates are larger in length relative to thickness so as to obtain the artifacts 161 of the metal plates 16 clearly without overlap on the artifact from the puncture needle 61 and the image of the puncture needle 6 itself.

Since two parallel artifacts 161 are displayed, it is possible to confirm whether the target 3 is positioned between the two parallel artifacts, and to prevent the inclination of the puncture needle 6 to the target 3.

When only the length of the pole brace 17 is changed and the length of the guide section 11 remains constant, the angle between the guiding device 10 and the body surface 2 is changed easily and the angle of the puncturing route can be varied. The three-dimensional adjustment of the guide section 11 for placing the target 3 between the two artifacts 161 can be achieved merely by changing the length of the pole brace 17.

In a preferred embodiment of the present invention, it may be considered for changing a length of a pole brace along the axial direction thereof that the pole brace standing erect in parallel to a guide section is modified to have such structure that the pole brace itself or leg itself is formed, for example, into a concentric sliding cylinders, or a structure wherein helical screws are used. Further, it may be considered that a structure wherein a leg being slidable vertically can be secured by fastening screws is applied to a pole brace, As the Other configurations, for example, a structure wherein a leg which can be slid vertically by means of a handle is attached to a pole brace whereby a length of the pole brace is changed vertically maybe adopted. In accordance with the above described measures, a guide section may be inclined by changing a length of a pole brace as a means for adjusting a puncturing direction (angle).

In a preferred embodiment of the present invention, other means for adjusting and setting an angle of a guide section, for example, a structure wherein an upper portion of a pole brace is formed into a ball shape, the ball-shaped upper portion is rotatably mounted on a beam, and it is fastened by means of a screw may also be considered, in addition to a structure wherein a pole brace is mounted adjustably to a beam in such a manner that a supporting angle of a bearing of the pole brace is controlled by means of screw mechanism. Moreover, there may be also a structure wherein a guide section is constituted to be movable within a range of a certain angle, whereby the angle can be adjusted by means of the guide section itself. In this case, a length of a guide section in the longitudinal direction thereof should be a length which does not be in contact with a subject's body surface with taking movability in the case where a pole brace is placed on the subject's body surface into consideration.

In a preferred embodiment of the present invention, as a means for adjusting a puncturing direction (adjustment of a puncturing angle) with respect to a target site, it has been exhibited that a puncturing direction with respect to a target site can be changed by moving a pole brace or a leg in the axial direction thereof, thereby changing a length of the pole brace based on a function of varying an amount of projection which has been prepared on the pole brace itself or the leg in a device for guiding a puncture needle.

Other than that described above, a structure by which a puncturing direction with respect to a target site is changed may be considered. For instance, there are a structure wherein a puncturing direction is rotated around a pole brace and a beam connecting section as the bearings to change freely an-angle, a structure wherein a puncturing direction is rotated around a guide section and a beam connecting section as the bearings to change freely an angle, and the like structure. Since beam connecting sections exist in both the ends of the beam, when it is constituted in such that a pole brace and a guide section can be rotated within a range of a certain angle, it is possible to change a puncturing direction with respect to a target site.

For example, in a preferred embodiment of the invention, a guide section, a pole brace, and a connecting section with a beam which connecting integrally both of the guide section and the pole-brace may be considered to constitute rotatably the same in at least either of the guide section and the pole brace, or both of them, After deciding a puncturing direction, movement in the rotatable connecting section of the guide section and the beam is secured by a fastening means.

As a result, it becomes possible to transfer the pole brace to an arbitrary position on the subject's body surface within a range defined by a circle wherein the center corresponds to the guide section and a radius corresponds to a length of the beam, when the examiner puts on a device for guiding a puncture needle on the subject's body surface.

As described above, when a guide section, a pole brace, and a beam for connecting integrally both these members are constituted rotatably, it becomes possible to transfer the device for guiding a puncture needle to an arbitrary position in the case when an puncturing operation is performed on a subject's body surface by using the guiding device. As a result, operability in manipulation to be performed by an examiner is elevated, whereby an exact puncturing operation is realized with respect to a target site, According to the device for guiding a puncture needle of a preferred embodiment of the invention, a bottom of a leg in a pole brace for keeping the guiding section standing erect in parallel thereto has a function for securing the guiding device to a subject's body surface. As a result, it becomes possible to positively hold the guiding device on the subject's body surface. In addition, since the leg of the pole brace is constituted in such that a length thereof is changeable vertically, it becomes possible to freely set a puncturing direction in conformity with a CT cross-section image. Thus, decision of such puncturing direction, and holding of the device after the decision become easy and positive. The device for guiding a puncture needle of the invention is easily secured to a subject's body surface, so that adverse affect due to movement of a subject's body decreases, In a preferred embodiment of the invention, since a leg for a pole brace standing erect in parallel to a guide section is provided with a sucker leg having sucking function and made of rubber or a plastic material, it becomes simpler to secure a device for guiding a puncture needle, which has been placed on a subject s body surface, to the very subject's body surface.

In a preferred embodiment of the invention, with respect to a beam (cross beam) for connecting a guide section with a pole brace standing erect in parallel to each other, it may be considered that a cross section of the beam is circular, elliptical, rectangular, or the like; and a configuration of which is plate, arch truss-shaped or the like. Thus, a desired strength can be maintained in the beam, and further, it becomes possible to obtain an integrally molded article made of a plastic material having a shape for which molding operation is easy.

In a preferred embodiment of the invention, other structures for a rotatable connecting section which connects a guide section, a pole brace, and a beam for connecting both these members with each other may be considered as an adjusting means for aligning the guide section to a target site (puncturing position). In this connection, these other structures are, for example, a concentric rotatable connecting section composed of a guide section and a cylindrical ring for a beam which is fabricated by such a manner that cylindrical rings are formed on the opposite ends of the beam, and the guide section and the pole brace are fitted in the cylindrical rings, respectively, whereby a concentric rotatable connecting section composed of the guide section and a cylindrical ring of the beam as well as another concentric rotatable connecting section composed of the pole brace-and a cylindrical ring of the beam. It is possible to dispose such concentric rotatable connecting section(s) at least either of the guide section and the pole brace, or at both the guide section and the pole brace.

Furthermore, a structure of a rotatable connecting section in case of involving two pole braces can be realized by connecting integrally two pole braces with a star type (Y-shaped) beam. For example, it may be considered that cylindrical rings are defined on three ends of the star type (Y-shaped) beam, respectively, and two pole braces and one guide cylinder having a lower height than that of the pole brace are fitted in these tree cylindrical rings. As a result, a concentric rotatable connecting section composed of the guide cylinder and the cylindrical ring of the beam as well as a concentric rotatable connecting section composed of two pole graces and two cylindrical rings of the beam can be formed, respectively.

When there are such concentric rotatable connecting sections, it becomes possible to stabilize a device for guiding a puncture needle by transferring the pole braces at any arbitrary positions on a subject's body surface within a range defined by a circle wherein the center corresponds to the guide cylinder and a radius corresponds to a length of the beam, when an examiner puts on the device for guiding a puncture needle on the subject's body surface. Similarly, it becomes possible to transfer the guide cylinder to the position of a target site within a range wherein each of pole braces corresponds to the fulcrum and a radius corresponds to a length of the beam. A variety of other types of mechanism can be applicable for such rotatable connecting sections as described above.

For an occasion where a position of a guide section is decided with respect to a target site, for example, a band for reducing an inside diameter of a cylindrical ring may have been previously prepared. First, a slit is defined in an upper or a lower portion of a cylindrical ring along the axial direction thereof, and then, a vicinity of the slit is fastened with the band. As a result, it becomes possible to tentatively prevent a movement of the rotatable connecting section to fix a position of the guide section.

In a preferred embodiment of the invention, it is required to prepare a device for guiding a puncture needle comprising a guide section, a pole bracer and a beam (cross beam) for connecting the guide section with the pole brace from a material which allows X-rays to pass through in order that an image of CT laminar plane (sliced plane, scanned plane) is not intercepted by these components of the guiding device, Namely, the guide section, the pole brace, and the beam for connecting these both members with each other may be molded articles each prepared from a plastic material such as a clear acrylic resin which allows X-rays to pass through when applied radiation thereto and does not produce any shadow in its image. When a device for guiding a puncture needle which has been prepared from a clear plastic material is employed, no extra shadow is produced in its image, so that examiner's observation during manipulation becomes easy.

In a preferred embodiment of the present invention, it is desired to mold a guide section, a pole brace, and a beam for connecting both the members in the form of an integrally molded article to the extent possible. More specifically, these members may be molded into an integrally molded article from a moldable plastic material such as a colorless clear acrylic resin. As a result of employing a moldable plastic material, an integrally molded article of the guide section, the pole brace, and the beam for connecting both the members is easily prepared.

Moreover, when a device for guiding a puncture needle being an integrally molded article prepared from a colorless clear plastic material is used, a function for feeling a wider visual range is attained, so that an examiner's visual range is widely maintained, whereby such a visual range in case of observing a subject's body surface by the examiner during his (or her) manipulation is easily assured.

In a preferred embodiment of the invention, with respect to the case where a device for guiding a puncture needle is used to puncture a subject's body at a target site with an introducer and a puncture needle, and then separate manipulation follows with keeping a needle tube punctured as it is, it is required to leave the needle tube, and to remove the guiding device. In this connection, the guiding device according to the present invention can comply with such request.

In a preferred embodiment of the invention, since a function for capable of opening and closing an insertion hole is allowed to give to a guide section in a device for guiding a puncture needle in order that the puncture needle can be removed from a subject's body surface with leaving the puncture needle in a punctured state, parallel separation of the guide section becomes possible in the longitudinal direction thereof. A guide section in a preferred embodiment is provided with a holding mechanism composed of a holding section which is openable in parallel to an insertion hole, or a holding section which is detachable. Accordingly, when it is intended to remove the guiding device, it may be taken such steps that the holding section in the guide section is opened to leave an introducer and the puncture needle contained in the insertion hole in a punctured state as they are, and that only the guiding section is taken away from the subject is body surface.

According to the device for guiding a puncture needle of the present invention, since a height of a guide section can be made lower, there are such advantages that a space under a gantry for CT in which manipulation for puncturing operation with a needle is to be carried out can be widely maintained, so chat manipulation for puncturing operation with a needle becomes easy in the guiding device, whereby exact puncture becomes possible with respect to a target site, and a period of time for manipulation can be reduced, Furthermore, according to the device for guiding a puncture needle of the invention, an introducer has been previously inserted into a guide section, and then the puncture needle can be inserted by utilizing the introducer at a position away from that under the gantry for CT which produces radiation.

Accordingly, there is such an advantage that a fear of exposure to radiation upon an examiner disappears even in case of puncturing operation under CT transmission. Besides, since a guide section through which a puncture needle is inserted is provided with a holding mechanism composed of a holding section wherein the insertion hole can be freely opened and closed, or a holding section being detachable, there is such an advantage that after a target site was punctured by a needle, a guiding section can be removed from a subject's body surface with leaving the puncture needle as it is.

Moreover, in the device for guiding a puncture needle, since a metallic thin sheet mounted on a guide section appears as a black line image in case of X-radiation under CT transmission, alignment of the guide section to a puncturing line can be exactly performed. As a result, an examiner sets easily and positively a device on a subject's body 'surface, whereby there is an advantage of capable of complying also with a movement of the subject's body.

In addition, since the device for guiding a puncture needle according to the present invention has a basic structure of a guide section, a pole brace, and a beam connecting both the members in parallel to each other in a standing erect state, it is easily molded into an integrally molded article, so that there are advantages of a simple structure and small number of parts in the guiding device.

It will be appreciated by those of ordinary skill in the art that the present invention can be embodied in other specific forms without departing from the spirit or essential characteristics thereof.

The presently disclosed embodiments are therefore considered in all respects to be illustrative and not restrictive. The scope of the invention is indicated by the appended claims rather than the foregoing description, and all changes that come within the meaning and range of equivalents thereof are intended to be embraced therein.

What is claimed is:

1. A device for guiding a puncture needle where a puncturing operation with the needle is performed percutaneously with respect to a target site in a subject in accordance with a target determined by image data obtained in CT (computerized tomography), comprising:
    a guide section having an insertion hole for an introducer and the puncture needle, and metal plates that create artifacts for indicating a puncturing route when radiation is applied,
    a pole brace that changes its length along an axial direction standing erect substantially parallel to said guide section and having a leg for securing said device for guiding a puncture needle to a subject's body surface, and
    a beam for connecting said guide section with said pole brace.

2. A device for guiding a puncture needle as claimed in claim 1, wherein:
    said guide section and said pole brace connected by means of said beam in which said guide section has a height equal with that of said pole brace, or said guide section has a lower height than that of said pole brace.

3. A device for guiding a puncture needle as claimed in claim 1, wherein:
    said pole brace is disposed at a position being substantially parallel to said guide section standing in an erect state, or two of said pole braces are disposed at positions apart from said guide section with equal distances, respectively.

4. A device for guiding a puncture needle as claimed in claim 1, wherein:
    said leg in said pole grace contains a suction leg having a function of suction disk ability by which said device for guiding a puncture needle can be secured to a subject's body surface when placed on the subject's body.

5. A device for guiding a puncture needle as claimed in claim 1, wherein;
    said beam for connecting said guide section with said pole brace contains a connecting section having a function by which said guide section or said pole brace can be rotated at either of an interconnecting section formed by said guide section and said beam, and an interconnecting section formed by said pole brace and said beam.

6. A device for guiding a puncture needle as claimed in claim 1, wherein:
    said interconnecting section formed by said guide section and said beam as well as said interconnecting section formed by said pole brace and said beam are provided, respectively, with a fastening function which can prevent tentatively a movement of said rotatable connecting section to fix a position of said guide section.

7. A device for guiding a puncture needle as claimed in claim 1, wherein:
    said beam for connecting both said guide section and said pole brace is prepared from a moldable plastic material or the like into an integrally molded article.

8. A device for guiding a puncture needle as claimed in claim 1, wherein:
    said beam for connecting both said guide section and said pole brace is composed of a molded article made of a plastic material or the like which allows X-ray to pass through the same and does not produce shadow in its image in case of applying radiation.

9. A device for guiding a puncture needle as claimed in claim 1, wherein:
    said guide section containing said insertion hole is provided with a holding mechanism of an openable holding section or of a detachable holding section along the longitudinal direction of said insertion hole in order that said device for guiding a puncture needle can be removed from said introducer and said puncture needle which have been inserted in said insertion hole.

10. A device for guiding a puncture needle as claimed in claim 1, wherein:
    the metal plates are positioned in parallel and opposite each other on the a guide section for creating parallel artifacts.

* * * * *